United States Patent [19]

Gasaway et al.

[11] Patent Number: 5,024,656
[45] Date of Patent: Jun. 18, 1991

[54] GAS-PRESSURE-REGULATED NEEDLELESS INJECTION SYSTEM

[75] Inventors: Jack S. Gasaway, Irvine; J. Stuart Parsons, Laguna Niguel; Robert L. Harshman, Chino Hills, all of Calif.

[73] Assignee: Injet Medical Products, Inc., Irvine, Calif.

[21] Appl. No.: 238,360

[22] Filed: Aug. 30, 1988

[51] Int. Cl.⁵ .............................................. A61M 5/00
[52] U.S. Cl. ..................................... 604/70; 604/68; 604/141
[58] Field of Search ................................... 604/68–72, 604/140, 141, 143, 147; 222/389

[56] References Cited

U.S. PATENT DOCUMENTS

| Re. 24,419 | 1/1958 | Ziherl et al. |
|---|---|---|
| 2,547,099 | 4/1951 | Smoot |
| 2,605,763 | 8/1952 | Smoot |
| 2,635,601 | 4/1953 | May |
| 2,635,602 | 4/1953 | Hein, Jr. |
| 2,645,223 | 7/1953 | Lawshe et al. |
| 2,650,591 | 9/1953 | Love |
| 2,653,603 | 9/1953 | Hein, Jr. |
| 2,653,605 | 9/1953 | Hein, Jr. |
| 2,667,871 | 2/1954 | Hein, Jr. |
| 2,680,439 | 6/1954 | Sutermeister |
| 2,687,725 | 8/1954 | Hein, Jr. |
| 2,695,611 | 11/1954 | Letac |
| 2,699,166 | 1/1955 | Dickinson, Jr. et al. |
| 2,704,543 | 3/1955 | Scherer |
| 2,737,946 | 3/1956 | Hein, Jr. |
| 2,764,977 | 10/1956 | Ferguson |
| 2,785,678 | 3/1957 | Hein, Jr. |
| 2,798,486 | 7/1957 | Hein, Jr. |
| 2,800,903 | 7/1957 | Smoot |
| 2,821,193 | 1/1958 | Ziherl et al. |
| 2,821,981 | 2/1958 | Ziherl et al. |
| 2,921,582 | 1/1960 | Sadd |
| 2,928,390 | 3/1960 | Venditty et al. |
| 3,045,659 | 7/1962 | Malcolm |
| 3,057,349 | 10/1962 | Ismach |
| 3,115,133 | 12/1963 | Morando |
| 3,123,070 | 3/1964 | Kath |
| 3,130,723 | 4/1964 | Venditty et al. |
| 3,131,692 | 5/1964 | Love |
| 3,138,157 | 6/1964 | Ziherl et al. |
| 3,167,071 | 1/1965 | Venditty |
| 3,202,151 | 8/1965 | Kath |
| 3,292,621 | 12/1966 | Banker |
| 3,292,622 | 12/1966 | Banker |
| 3,330,276 | 7/1967 | Gordon |
| 3,406,684 | 10/1968 | Tsujino |
| 3,424,154 | 1/1969 | Kinsley |
| 3,425,413 | 2/1969 | Stephens |
| 3,461,867 | 8/1969 | Zimmet et al. |
| 3,515,130 | 6/1970 | Tsujino |
| 3,518,990 | 7/1970 | Banker |
| 3,521,633 | 7/1970 | Yahner |

(List continued on next page.)

FOREIGN PATENT DOCUMENTS 569887 2/1959 Canada .
0971162 9/1964 United Kingdom ................. 604/70

OTHER PUBLICATIONS

Flyer entitled, "Preci-Jet 50", (undated), Advanced Medical Technologies, Inc.
Flyer entitled, "Medi-Jector II", (undated), Derata Corporation.
Flyer entitled, "Preci-Jet 50", (undated), Home Diagnostics, Inc.
510(K) Notification–Derata Medi-Jector II–Supplemental Report (no date).

Primary Examiner—Stephen C. Pellegrino
Assistant Examiner—Ralph A. Lewis
Attorney, Agent, or Firm—Christie, Parker & Hale

[57] ABSTRACT

A system is provided that is useful for hypodermic injection of medication without piercing the skin with a needle. The system includes a gas pressure actuated needleless hypodermic injection device for injecting medication through the skin. The injection device includes an injector assembly having an injector body with a chamber for a compressed gas container and an ampule assembly mounted on the injector body for containing the liquid medication. The system also includes an adaptor assembly for use on a medication vial for transferring medication to the ampule assembly.

38 Claims, 8 Drawing Sheets

U.S. PATENT DOCUMENTS

| | | |
|---|---|---|
| 3,526,225 | 9/1970 | Isobe . |
| 3,561,443 | 2/1971 | Banker ................................ 604/70 |
| 3,688,765 | 9/1972 | Gasaway . |
| 3,695,266 | 10/1972 | Lussier . |
| 3,714,943 | 2/1973 | Yanof et al. . |
| 3,763,859 | 10/1973 | Yanof et al. . |
| 3,788,315 | 1/1974 | Laurens . |
| 3,805,783 | 4/1974 | Ismach . |
| 3,815,594 | 6/1974 | Doherty . |
| 3,853,125 | 12/1974 | Clark et al. . |
| 3,859,996 | 1/1975 | Mizzy et al. . |
| 3,908,651 | 9/1975 | Fudge . |
| 3,933,155 | 1/1976 | Johnston . |
| 3,945,379 | 3/1976 | Pritz et al. . |
| 3,945,383 | 3/1976 | Bennett et al. . |
| 4,004,575 | 1/1977 | Sarstedt . |
| 4,031,889 | 6/1977 | Pike . |
| 4,059,107 | 11/1977 | Iriguchi et al. . |
| 4,089,334 | 5/1978 | Schwebel et al. . |
| 4,103,684 | 8/1978 | Ismach . |
| 4,124,024 | 11/1978 | Schwebel et al. . |
| 4,301,795 | 11/1981 | Zimmermann . |
| 4,342,310 | 8/1982 | Lindmayer et al. . |
| 4,400,172 | 8/1983 | Dettbarn et al. . |
| 4,403,609 | 9/1983 | Cohen . |
| 4,421,508 | 12/1983 | Cohen . |
| 4,426,024 | 1/1984 | Hogan et al. ................... 604/141 |
| 4,447,225 | 5/1984 | Taff et al. . |
| 4,507,113 | 3/1985 | Dunlap . |
| 4,518,385 | 5/1985 | Lindmayer et al. . |
| 4,592,742 | 6/1986 | Landan . |
| 4,596,556 | 6/1986 | Morrow et al. . |
| 4,680,027 | 7/1987 | Parsons et al. . |

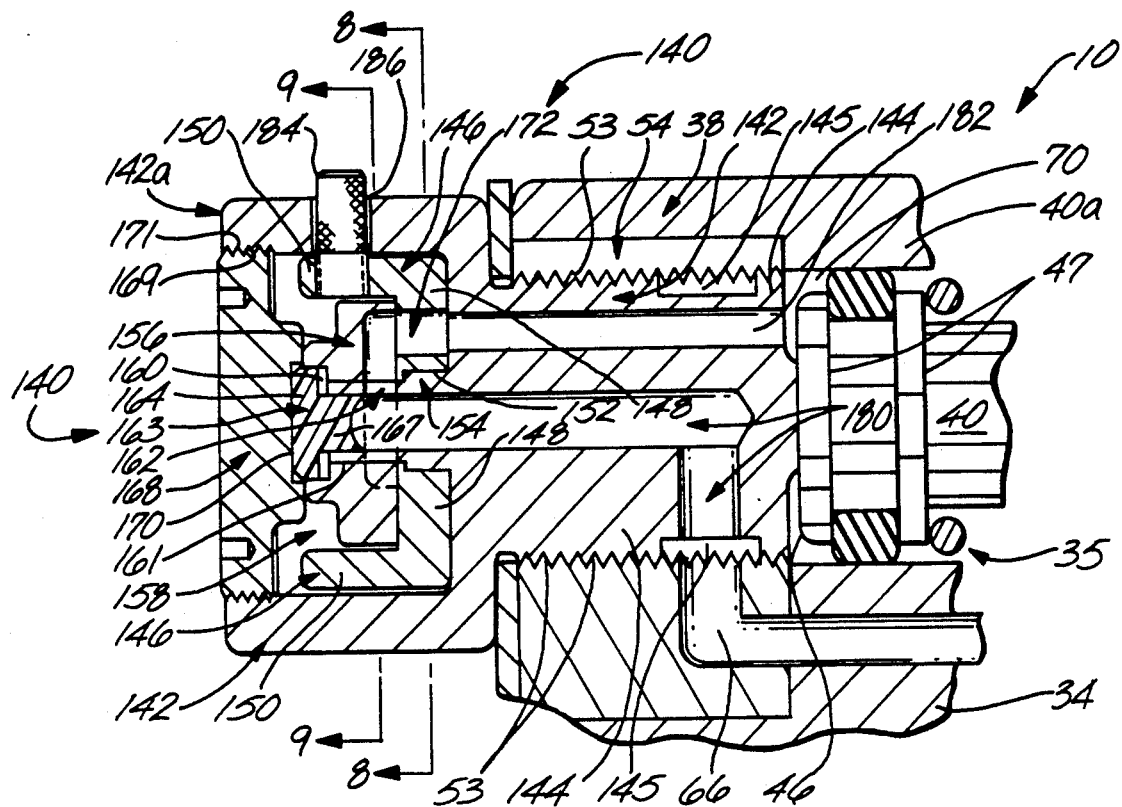
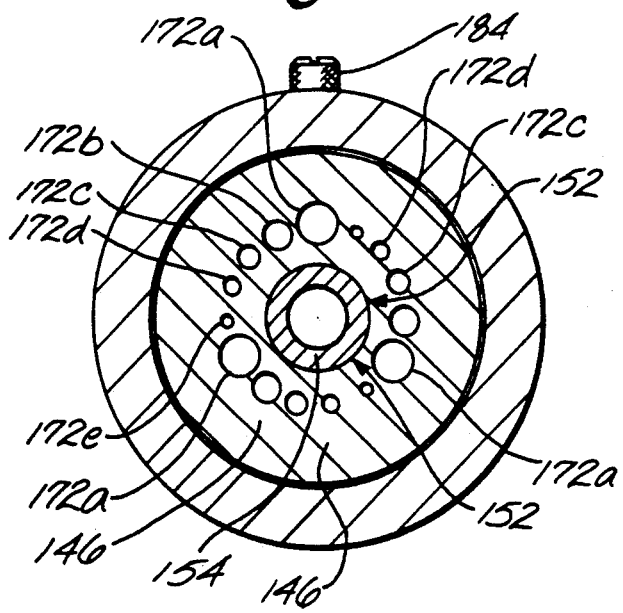
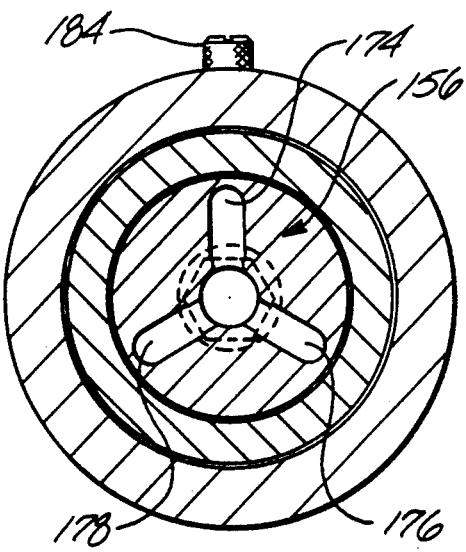

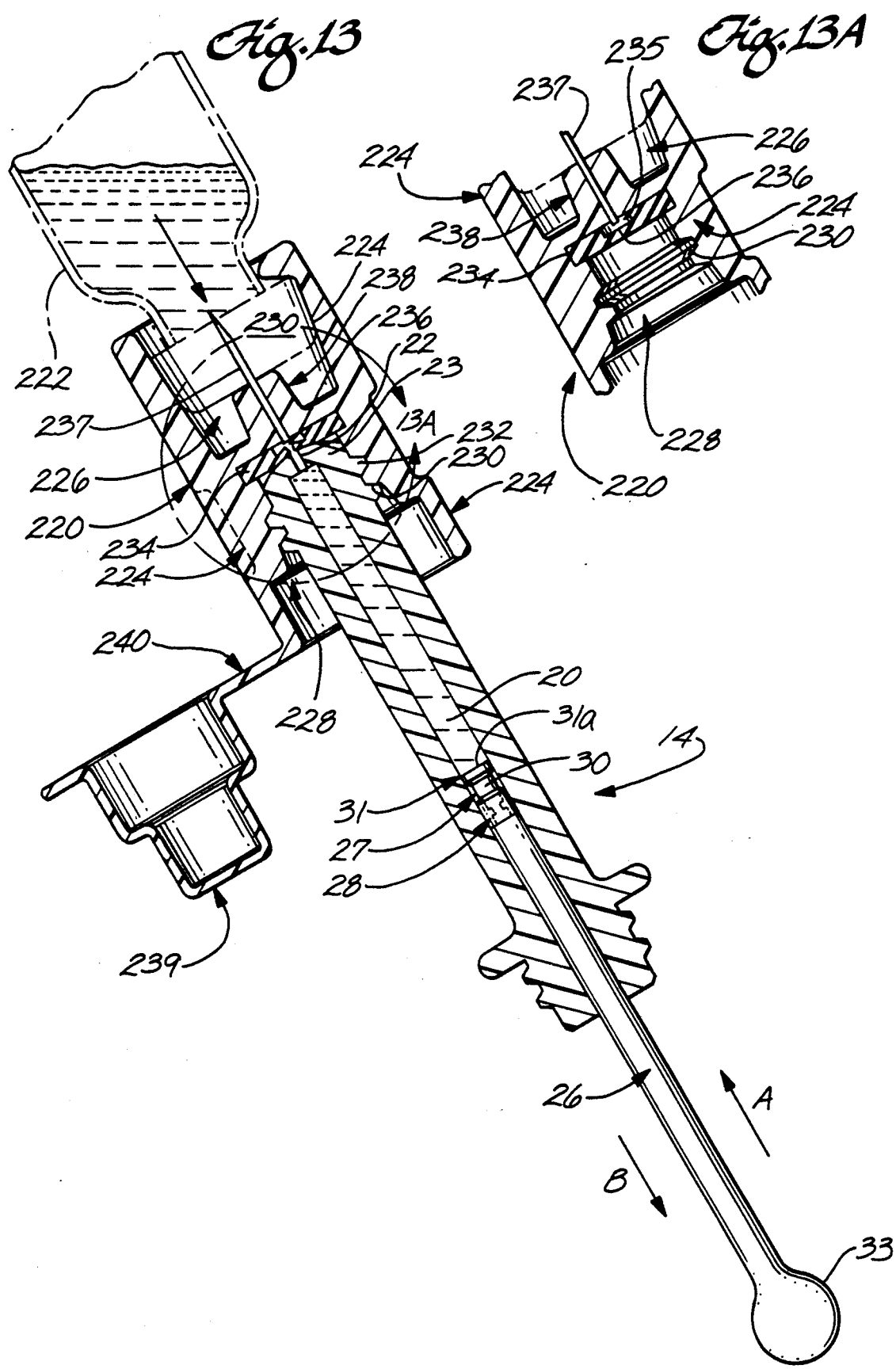

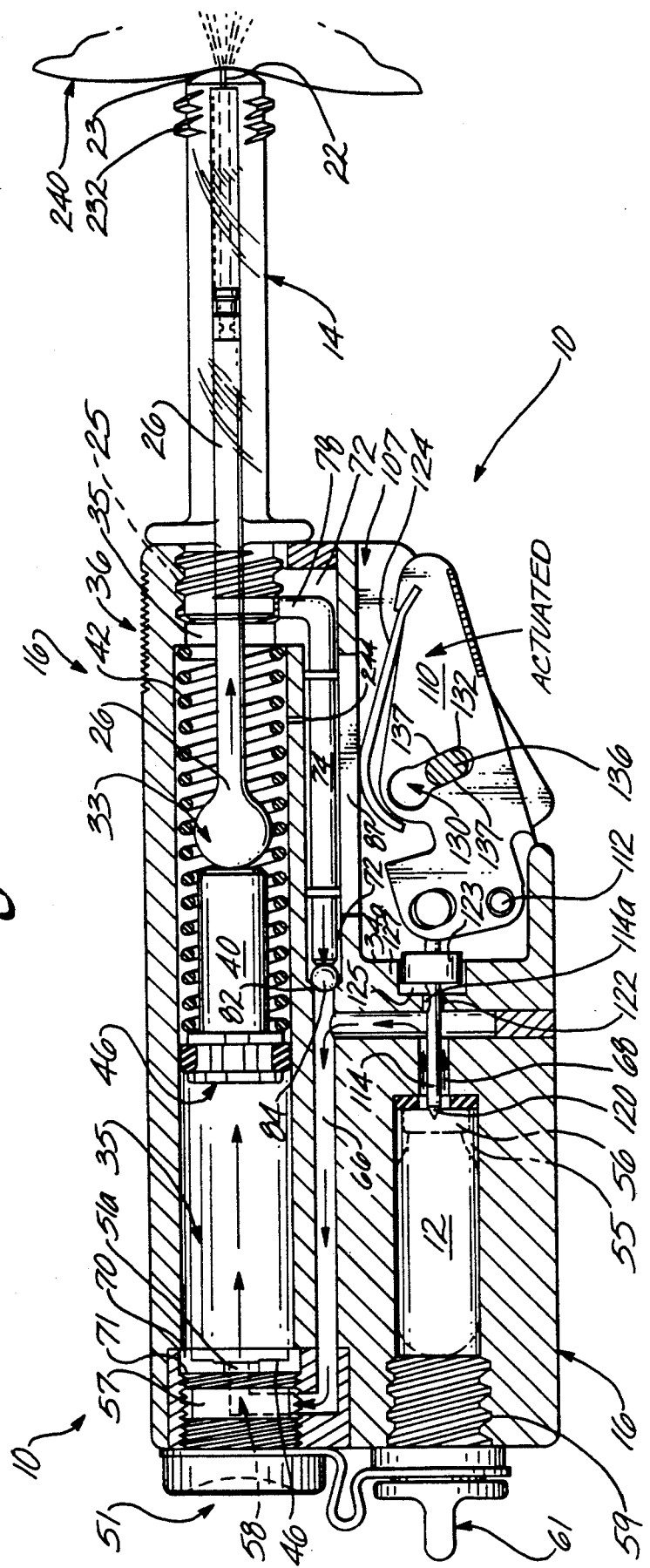

GAS-PRESSURE-REGULATED NEEDLELESS INJECTION SYSTEM

FIELD OF THE INVENTION

This invention relates to a system for providing hypodermic injection of medication without piercing the skin with a needle.

BACKGROUND OF THE INVENTION

Various systems for use in providing hypodermic injection of medication without piercing the skin with a needle are known in the art. Such systems can include hypodermic injection devices powered by pressurized gas.

One such needleless hypodermic injection device is disclosed in U.S. Pat. No. 4,680,027 which issued on July 14, 1987 to James S. Parsons and Jack S. Gasaway. This device includes a disposable syringe which can be inserted into a power supply mechanism. The syringe has a cavity for holding liquid medication and an aperture on one end through which liquid medication can flow into and out from the cavity. A plunger is in the cavity for drawing liquid medication into the cavity and for forcing the liquid medication out from the cavity. The syringe has a hollow, tubular needle removably attached to it with the needle in alignment with the aperture in the end of the syringe. The needle is insertable into a container of liquid medication so that the syringe can be filled by pulling on the plunger in a conventional manner. The needle is removable from the syringe after the liquid medication has been drawn into the syringe so that the aperture in the end of the syringe can be placed in direct contact with the skin.

The power supply mechanism has a trigger which, when pulled, unseals a container of compressed gas to release the gas. The released gas provides a force to move the syringe plunger toward the aperture so that the liquid medication is ejected through the aperture with sufficient force to penetrate the skin. The pressure applied to the liquid medication can be varied by changing the spring constant of a spring which might be used, or by adjusting a needle valve to reduce the flow of gas to the piston.

The above-described power supply mechanism includes safety interlocks, one of which prevents securing the syringe within the power supply mechanism until the needle is removed. A second interlock prevents movement of the trigger so that the gas container cannot be opened unless the syringe is fully secured in the power supply mechanism. Both interlocks are relatively complex mechanical systems.

It is desirable to provide a needleless hypodermic injection device with a relatively simple, easy-to-use, and reliable system for varying the gas pressure applied to the liquid medication so that the medication can be ejected at a desired velocity. Such reliable ejection velocity control can be important, for example, because discomfort is minimized when the minimum velocity required to appropriately penetrate the skin is used. Minimum required velocities can be different for different injection locations, and more or less gas pressure can be required to attain the minimum required velocity when medications of different viscosities are injected.

There is a need for a needleless hypodermic injection device which has an enhanced simplicity of design, including a simple design of the interlock mechanisms, but yet which provides for improved user comfort by incorporating a reliable system for adjusting medication ejection velocity.

SUMMARY OF THE INVENTION

This invention relates to a system for providing hypodermic injection of medication. The system includes (1) a pressure actuated needleless hypodermic device of simple, efficient and reliable design for injecting variable doses of liquid medication at selected velocities through the skin of a person or animal and (2) an adaptor assembly for use on a medication vial for transferring medication to the injection device.

The pressure actuated needleless hypodermic injection device includes an ampule assembly having a body with a cavity for holding liquid medication and an injector assembly for receiving and mounting the ampule assembly. The ampule assembly preferably is disposable, but reusable ampules can be provided, if desired. A small orifice is in the front end of the ampule body through which liquid medication can flow into and out from the cavity. A plunger, movable within the cavity, is used for drawing the liquid medication into the cavity and for forcing the liquid medication out from the cavity.

The injector assembly provides a force to move the ampule assembly plunger to thereby force liquid medication through the ampule assembly orifice and into the skin. The injector assembly includes an injector body having a barrel closed at its back end and open at its forward or front end, wherein the front barrel end is configured to receive one end (the back end) of the ampule assembly to thereby externally mount the ampule assembly on the injector body. A piston, mounted to slide in the barrel, is pushed by gas pressure from its at-rest position at the back end of the barrel toward the front end of the barrel. A chamber is in the injector assembly configured to house a gas container or cylinder which, when opened, provides the pressurized gas to move the piston. A first passageway is in the injector assembly through which gas flows from the gas container to the barrel to thereby provide a force on the rearward-facing surface of the piston to move the piston forward toward the front end of the barrel.

Means are provided for releasing gas from the gas container to provide the force on the rearward-facing surface of the piston to thereby move the piston forward and into contact with the ampule assembly plunger.

Means are also provided for venting gas released from the gas container to the atmosphere when the ampule assembly end is not fully mounted or inserted in the injector assembly barrel. The piston moves the ampule assembly plunger toward the orifice to thereby eject the liquid medication from the cavity through the orifice.

In one embodiment, the gas venting means is a second passageway configured to be open to the atmosphere when the end of the ampule assembly is not fully mounted or inserted in the injector assembly barrel. In this embodiment, means are provided for sealing the second passageway to prevent venting gas through the passageway to the atmosphere when the ampule assembly end is fully mounted in the injector assembly barrel. In a preferred embodiment, the sealing means comprise a valve stem mounted in the second passageway for sliding movement along the length of the passageway. The valve stem is an L-shaped rod, with the forward end of the valve stem having a bend extending into the opening in the front end of the injector body barrel. A valve seat is on the upstream end of the second passageway, and a ball is located between the valve seat and the back or rearward-facing end of the valve stem. The front end of the valve stem engages the back end of the ampule assembly body as the assembly is being mounted in the barrel to thereby move the valve stem toward the valve seat during the mounting operation. When the end of the ampule assembly is fully mounted or inserted into the barrel, it holds the valve stem in place at its rearmost position which, in turn, traps the ball in gas-sealing engagement on the valve seat.

In a second embodiment, the gas venting means is an opening through the injector body configured to be open to the atmosphere when the ampule assembly end is not fully mounted or inserted in the injector assembly barrel. In this embodiment, means are provided for sealing the injector body opening to prevent venting gas through the injector body opening to the atmosphere when the ampule assembly end is fully mounted or inserted in the barrel. The sealing means comprises a valve seat on the outlet end of the injector body opening. A slide is mounted in the injector body for movement toward and away from the valve seat. A pin extends vertically from the front end of the slide into the opening in the forward end of the injector body barrel. A ball is located between the valve seat and the back end of the slide. Means are on the end of the ampule assembly to engage the pin as the assembly end is being mounted or inserted in the barrel to move the slide toward the valve seat during the mounting operation. When the ampule assembly is fully mounted, i.e., when its end has been fully inserted into the open front end of the barrel, it holds the slide in place at its rearmost position which, in turn, traps the ball in gas-sealing engagement on the valve seat.

In a preferred embodiment, the hypodermic injection device comprises means for varying the force of the gas that acts on the piston to thereby vary the velocity of the medication as it is ejected through the ampule assembly orifice. In one embodiment, the force-varying means comprises a gas-flow-regulator assembly comprising a disk having a plurality of gas-flow-restricting orifices of different sizes therethrough mounted in the injector body. The location of the disk is such that gas released from the container must pass through at least one such gas-flow-restricting orifice prior to contacting the piston. The flow-restricting orifices are configured to be selectively positioned in the gas flow path by rotating the disk.

In another preferred embodiment of the hypodermic injection device provided in accordance with this invention, the force-varying means comprise a gas-flow-regulator assembly that includes a throttle valve having a valve seat in the gas flow path between the gas container and the piston, and a ball or other sealing means, such as a plug, for engagement with the valve seat. A spring is provided for biasing the ball onto the seat with the spring tension capable of adjustment to hold the ball on the seat with more or less force as desired.

The adaptor assembly for use on a medication vial for transferring medication to the injection device comprises an assembly body which has two cavities spaced apart from each other on opposite ends. The first cavity is configured to receive the cap on a standard vial of liquid medication. The second cavity is configured to engage the end of the ampule assembly.

A diaphragm made of resilient plastic or rubber, or other suitable material, is mounted at the bottom of the second ampule body cavity. The diaphragm has a circular recess formed through a portion of its center adjacent the first cavity and hole through its center registered with the circular recess. The hole is closed when the ampule assembly is not in the second cavity, and is configured to be opened by the end of the ampule assembly when the ampule assembly is fully mounted in the second cavity. The diaphragm provides a liquid-tight seal between the end of the ampule assembly and the adaptor assembly when the ampule assembly is mounted therein.

A hollow, tubular needle extends through the center of the portion of the adaptor body that separates the first and second adaptor body cavities from each other. The top opening of the needle is positioned in the circular diaphragm recess with the point extending a sufficient distance into the first adaptor body cavity so that the medication vial cap is pierced by the needle when the adaptor is on the vial.

BRIEF DESCRIPTION OF THE DRAWINGS

These and other features, aspects and advantages of the present invention will be more fully understood when considered with respect to the following detailed description, appended claims, and accompanying drawings, wherein:

FIG. 7 is a semi-schematic, fragmentary, cross-sectional side view of the needleless hypodermic injection device of FIG. 1, having mounted thereon a gas-flow-regulator assembly provided in accordance with one embodiment of practice of this invention;

FIG. 8 is a semi-schematic, cross-sectional view of the flow-regulator device taken on line 8—8 of FIG. 7;

FIG. 9 is a semi-schematic, cross-sectional view of the flow-regulator device taken on line 9—9 of FIG. 7;

FIG. 13 shows a method for filling an ampule from a vial of liquid medication by means of an adaptor assembly provided in accordance with practice of principles of this invention;

FIG. 13A is an enlarged view of the adaptor assembly (without the ampule mounted therein) taken on line 13A of FIG. 13; and FIG. 14 shows activation of one embodiment of the device provided in accordance with this invention for ejecting liquid medication for hypodermic injection.

DETAILED DESCRIPTION

This invention relates to a system for providing hypodermic injection. The system components include a pressure actuated needleless hypodermic injection device (which comprises an injector assembly, a medication ampule assembly, and a gas container) and an adaptor assembly for use on a medication vial for transferring medication from the vial to the medication ampule assembly of the injection device.

Figure 1:
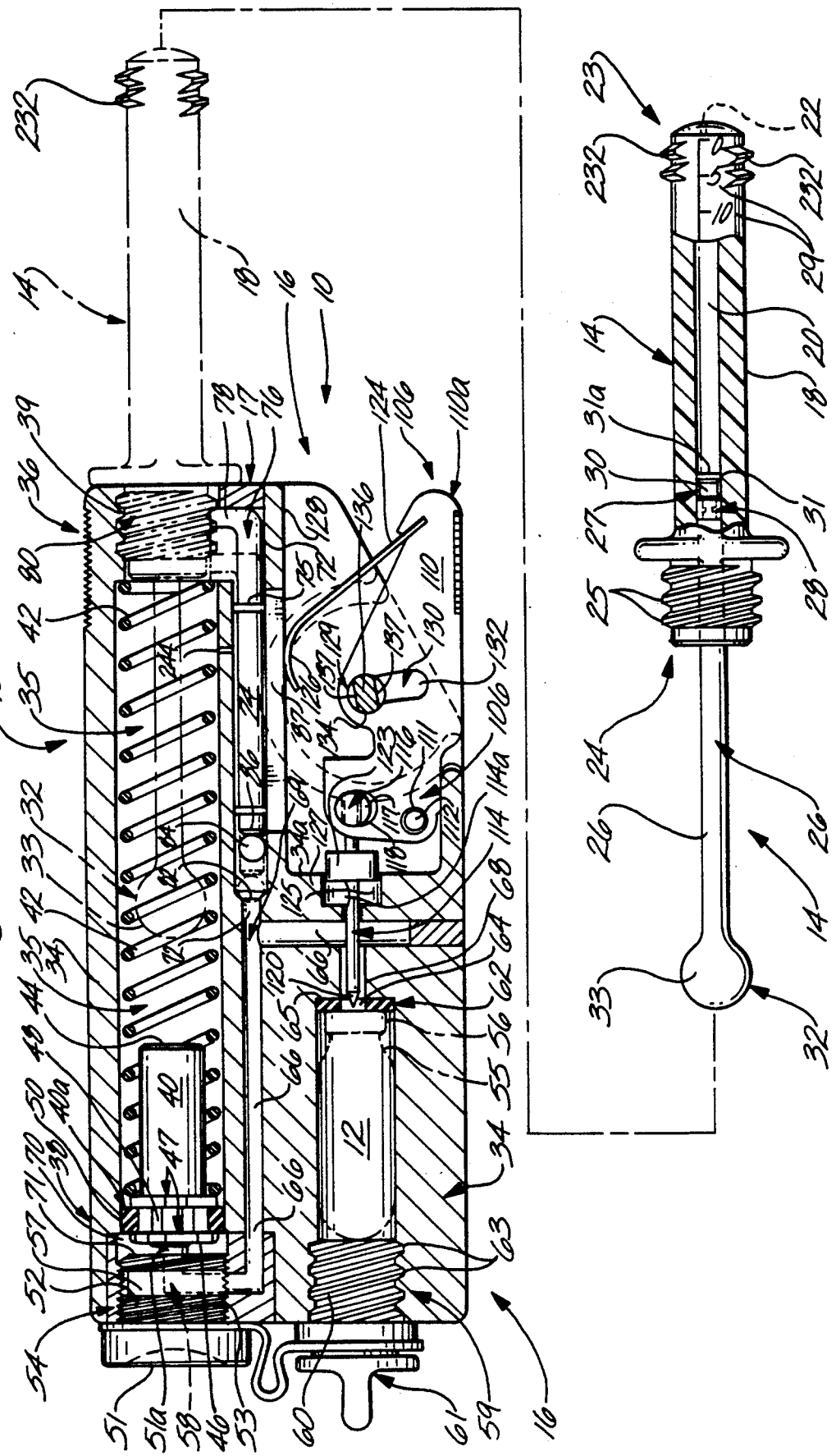
FIG. 1 is a semi-schematic, exploded side view, in partial cross-section, of an exemplary embodiment of a pressure actuated needleless hypodermic injection device provided in accordance with practice of this invention incorporating a first embodiment of a safety device for venting gas.

Referring to FIG. 1, there is shown a semi-schematic, exploded side view, in partial cross-section, of an exemplary embodiment of the pressure actuated needleless hypodermic injection device 10 provided in accordance with practice of principles of this invention. The injection device 10 comprises a disposable compressed gas container or cylinder 12, an ampule assembly 14, and an injector assembly 16. The disposable gas container 12 is configured to be mounted in the injector assembly 16 and the ampule assembly 14 is configured to be mounted externally on the injector assembly. The gas container 12 and ampule assembly 14 operate in conjunction with the injector assembly 16 to eject liquid medication from the ampule assembly 14 for hypodermic injection. The ampule assembly is preferably disposable, i.e., it is used only once and discarded. However, reusable ampule assemblies can be provided, if desired.

Although the injection device 10 can be held in any position, the positions of the components of the device relative to each other are described below with the ampule assembly 14 considered to be mounted on the front end 17 of the injector assembly 16. The top and bottom of the device are described as shown in FIG. 1 of the drawings.

The ampule assembly 14 comprises an elongated tubular body portion 18 having an elongated cavity 20 centrally disposed along the length of the body 18 for holding liquid medication (not shown). Although the body 18 can be made of a clear plastic by injection molding, other suitable materials, such as glass, can be used if desired. An orifice 22 is in the first or front end 23 of the body 18 and is in communication with the elongated cavity 20 so that liquid medication can flow into and out from the cavity through the orifice. In one embodiment, the back end 24 of the ampule body 18 is provided with threads 25 which, as described below in detail, are used for mounting the ampule assembly on the injector assembly 16. The threads 25 are preferably designed to provide a quick release of the ampule assembly from the injector assembly. Alternatively, the end 24 of the ampule body can be provided with a bayonet-type connection for engagement with an appropriately designed bayonet receptacle in the front end of the barrel.

A plunger assembly 26, comprising a plunger rod 26a, having a piston 27 mounted on its forward end 28, is in the cavity 20 and is movable within the cavity for drawing liquid medication into the cavity through the orifice 22 and for forcing the liquid medication out from the cavity through the orifice. The piston is preferably made of a flexible material such as rubber or plastic, or the like. Graduations 29 are provided on the body 18 so that the user can determine the exact amount of medication contained in the ampule. In a preferred embodiment, the piston 27 has a groove 30 around its forward end so that a flange portion 31, having a flat front face 31a, is provided on its front end. The piston preferably has an outside diameter which is slightly larger than the inside diameter of the cavity 20 so that the piston is compressed when the plunger assembly 26 is in the cavity 20. Thus, the piston forms an air- and fluid-tight seal between the plunger assembly and the walls of the cavity 20. When medication is in the ampule assembly, filling it to the piston flange 31, the flange indexes with the graduations 29 to indicate the amount of medication contained in the ampule.

The second end 32 of the plunger assembly extends out from the cavity 20, and is preferably enlarged to provide a head 33 that can be gripped by a person using the ampule, and to which a force can be applied to move the plunger assembly 26 forward to eject medication through the orifice 22. In a preferred embodiment of the injector assembly 10, the plunger head 33 is ball-shaped. The plunger head can be other than ball-shaped, if desired.

The injector assembly 16 is configured to receive and securely hold the ampule assembly 14 when the ampule assembly is filled with liquid medication, and to provide a force to move the plunger assembly 26 forward toward the orifice 22. Moving the plunger assembly 26 forward forces the liquid medication through the orifice 22 and into the skin of a person or animal receiving the hypodermic injection. The injector assembly 16 comprises a body portion 34 which includes an elongated barrel 35, open at its forward or front end 36 and closed at its back end 38. The barrel front end 36 is configured to receive and mount the ampule assembly 14. In an exemplary embodiment, threads 39 are provided in the front end 36 of the barrel 35 which mate with the threads 25 on the ampule body to provide a mounting for the ampule in the injector assembly 16. In a preferred embodiment, the threads 25 and mating threads 39 are special "quick release" threads so that the ampule assembly can be mounted or removed with minimal turning. For example, in one embodiment, the ampule assembly can be fully mounted or removed by turning it only one-half turn or 180°. The injector assembly body 34 can be formed of metal or suitable plastics, as desired.

A piston 40, which is resiliently biased toward the back end 38 of the barrel 35 by a coil spring 42, is mounted in the barrel 35 for sliding movement along its length. The piston 40 has a front-facing surface 44 which is preferably concave. If desired, the front-facing surface can be flat or can have other shapes. The piston surface 44 is aligned with the head 33 of the plunger assembly 26 when the ampule 14 is mounted in the barrel 35. The piston 40 has a second or rearwardly-facing surface 46 on which gas from the container 12 acts to push the piston forward. In the illustrated embodiment, the piston 40 has two raised rings 47 spaced apart from each other to form an annular cavity 48 around its end 40a. A Quad-ring 50, or other form of a seal, such as an O-ring, or the like, is seated in the cavity 48. The sealing ring as a slightly larger diameter than the inner diameter of the barrel 35 to provide a gas-tight fit between the piston and the interior barrel walls.

Access to the back or closed end 38 of the barrel 35 is provided by means of a removable plug 51 which has threads 52 on its end for engagement with threads 53 in an openings 54 through the back end of the injector body 34 to form a gas-tight closure. The plug 51 has a groove 57 around its circumference. A bore 58 extends from the groove 57 through the plug opens out of the center of the plug base. In the illustrated embodiment, the bore 58 exits the plug through a cylindrical extension 51a at the center of the plug base. The extension 51a provides a stop to limit the rearward motion of the piston in the barrel.

The disposable container or cylinder 12 containing compressed air, such as $CO_2$, is in a chamber 55 formed in a rear portion of the injector body 34 parallel to and below the barrel 35. Having a design where the chamber 55 is parallel to and below the barrel 35 minimizes the length of the device and makes it more compact. Although the container 12 in the illustrated embodiment has the shape of a standard $CO_2$ cylinder with a frangible cap or seal 56 on its front-facing end, containers having other shapes can be used, if desired. The container 12 can be made of metal or plastic. The frangible seal 56 on the cylinder is designed to be punctured to allow gas to escape from the cylinder as the device 10 is actuated to provide the force for the hypodermic injection. In an exemplary embodiment, gas cylinders can be placed into and removed from the chamber 55 through an opening 59 that extends through the back end of the injector body 34 below the opening 54 in which the plug 51 is mounted. The opening 59 has special quick release threads 63, similar to the threads 25 and 39 on the ampule assembly 14 and front barrel end 36, respectively, which engage quick release threads 60 on a plug 61 when the plug is in place in the opening 59. The plug 61 can be removed to open the chamber 55 so that an expended gas cylinder can be quickly removed and a new cylinder installed. When the plug 61 is in place in the opening 59, it urges the gas cylinder 12 forward against a resilient gasket 62, having an opening 64 through its center and mounted in the front end of the chamber between the gas cylinder seal 56 and the front chamber wall 65. Thus, the plug 61 provides for a secure, gas-tight mounting for the gas cylinder 12 in the chamber 55.

A first passageway 66 is provided in the injector body 34 through which gas flows to the back end 38 of the barrel 35 from the gas cylinder 12. Gas flows from the cylinder 12, through the gasket opening 64, and through an outlet 68 lined up with the opening 64 and extending from the chamber 55 into the passageway 66. In one exemplary embodiment, the passageway 66 extends vertically from the chamber outlet 68 to a "T" connection 69. The passageway 66 extends horizontally toward the back end of the injector body 34 from the "T" connection and then upwardly, opening into the groove 57 in the plug 51. The groove 57 opens into the bore 58, which opens into a cavity 70 between the forward-facing surface 71 of the plug 51 and the rearward-facing surface 46 of the piston 40. A second passageway 72 extends forward from the "T" connection 69 within the body 34. The passageway 72 is configured to be open for venting gas released from the gas cylinder 12 to the atmosphere through the front end 36 of barrel 35 when the end 24 of the ampule assembly 14 is not fully mounted or inserted in the barrel.

Means are provided for sealing the second passageway 72 to prevent venting gas through the passageway 72 to the atmosphere. The seal is provided only when the ampule assembly 14 is fully mounted on the injector assembly barrel, i.e., when the threaded end 24 of the ampule assembly is screwed tightly into the threaded front end 36 of the barrel 35. When gas from the cylinder 12 is vented to the atmosphere through the passageway 72, the gas pressure in the injector assembly does not increase to a sufficient level to move the piston 40 forward against the spring 42. Thus, the injector assembly cannot be used as a power source for a pencil or other potential projectile which may be inserted into the barrel 35 when the ampule assembly is not installed. This is an important safety interlock feature which ensures that foreign objects cannot be shot from the injector assembly.

In an exemplary embodiment, means for sealing the passageway 72 comprises a valve stem 74 mounted for sliding movement along the length of the passageway 72. The valve stem 74 rides in the passageway 72 on two rings 75 spaced apart on the valve stem along its length. More than two rings 75 can be used, if desired. The valve stem 74 is an L-shaped rod, with the first or forward end 76 of the valve stem having a 90° bend in it so that a portion 78 of the valve stem extends upwardly into the opening 80 in the forward barrel end 36. A valve seat 82 is at the back or upstream end of the passageway 72 adjacent the "T" connection 69. A resilient ball 84 is located between the valve seat 82 and the second or rearward-facing end 86 of the valve stem. If desired, a plug can be used in place of the ball 84. The upwardly-extending portion 78 of the valve stem 74 is configured to engage the threaded end 24 of the ampule assembly 14 as it is being screwed into the forward end 36 of the barrel 35. As the end 24 of the ampule assembly is screwed into the barrel 35, it engages the portion 78 of the valve stem 74 and thereby pushes the valve stem rearwardly toward the valve seat 82. The ball 84 rides over a slot 87 along the bottom of the passageway 72 as it is pushed rearwardly by the valve stem 74. When the ampule assembly 14 is fully mounted, i.e., when it has been screwed tightly into the barrel 35, it holds the valve stem 74 in place at its rearmost position in the passageway 72 to thereby hold or trap the ball 84 in gas-tight sealing engagement on the valve seat. When the ball is on the valve seat, gas released from the cylinder 12 cannot vent through the passageway 72 but, instead, is directed through the first passageway 66 into the chamber or cavity 70 to act on the rearward-facing surface 46 of the piston 40.

Figure 2:
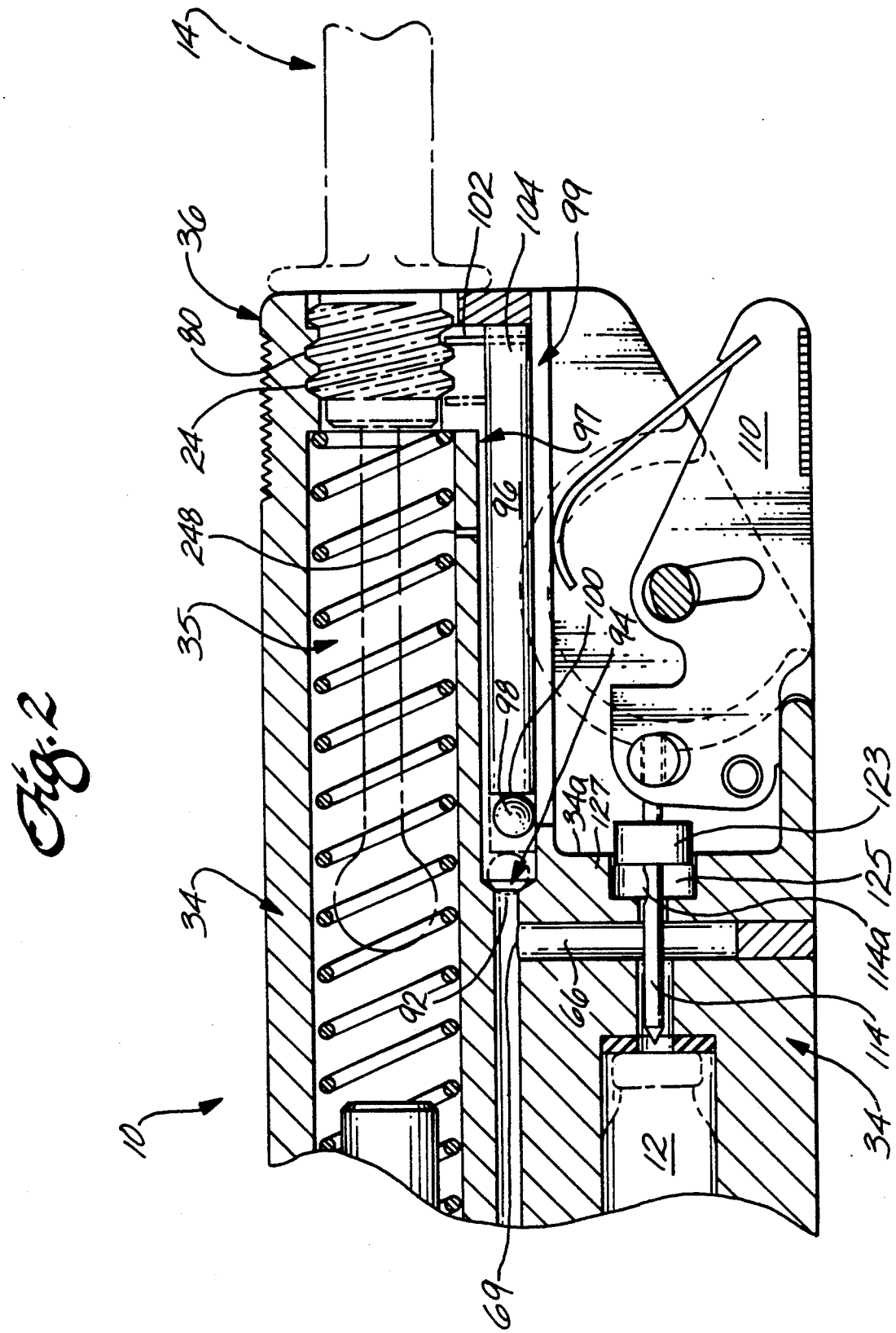
FIG. 2 is a semi-schematic, fragmentary, exploded side view of the pressure actuated needleless hypodermic injection device of FIG. 1, incorporating a second embodiment of a safety device for venting gas.

Referring to FIG. 2, a semi-schematic, fragmentary side view, in partial cross-section, of the hypodermic injection device 10 of FIG. 1 is shown, incorporating a second embodiment of a safety device for venting gas to the atmosphere when the ampule assembly 14 is not mounted in the barrel 35. In this embodiment, an opening 92 extends from the "T" connection 69 through the injector body 34 to the atmosphere. The opening 92 is configured to be open when the end 24 of the ampule assembly 14 is not fully mounted or inserted in the forward end 36 of the barrel 35. Means are provided for sealing the opening 92 to prevent venting gas to the atmosphere when the ampule assembly 14 is fully mounted. The gas-sealing means include a valve seat 94 on the outlet end of the injector body opening 92, a slide 96 mounted in the injector body 34 for movement in a horizontally-extending elongated cavity 97 in the front end of the injector body toward and away from the valve seat, and a resilient ball 98 located between the valve seat 94 and the back or rearward-facing end 100 of the slide 96. If desired, a plug can be used in place of the ball 98. A pin 102 extends vertically from the front end 104 of the slide 96 into the opening 80 in the barrel forward end 36. As the ampule assembly is screwed into the barrel, the threaded end 24 of the assembly 14 engages the pin 102 and thereby pushes the slide 96 rearwardly along the length of the injector body 34 toward the valve seat 94. The ball 98 rides over a slot 99 along the bottom of the cavity 97 as it is pushed rearwardly by the slide 96. When the ampule assembly 14 has been screwed tightly into the barrel 35, it holds the slide 96 in place at its rearmost position to thereby hold or trap the ball 98 in sealing engagement on the valve seat 94.

Figure 3:
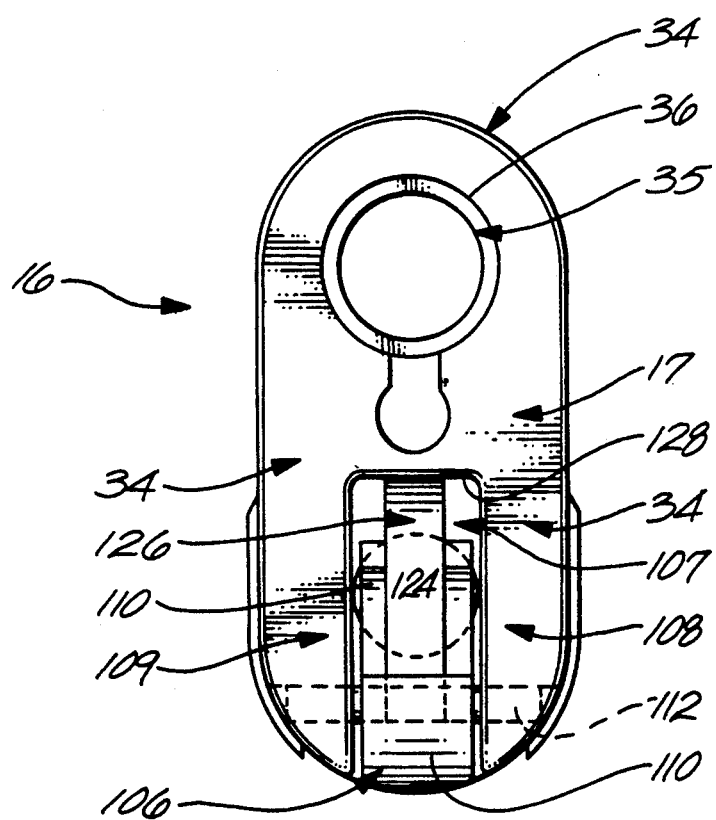
FIG. 3 is a semi-schematic front view of the needleless hypodermic injection device shown in FIG. 1 without the ampule assembly portion.

Referring again to FIG. 1, and to FIG. 3, which is a semi-schematic front view of the injection device 10, without the ampule assembly 14 mounted thereon, the injector assembly 16 includes an actuator assembly 106 mounted on the injector body 34 for releasing gas from the gas cylinder 12. The actuator assembly 106 is in a slot 107 formed by side walls 108 and 109 of the body 34 located below the barrel 35 and forward of the gas cylinder chamber 55. The actuator assembly includes an actuating lever 110, having a circular opening 111 through its bottom rear portion configured to receive a pin 112 that extends between the side walls 108 and 109 perpendicular to the length of the injector body. The pin 112 is through the opening 111 so that the actuating lever 110 can be pivoted on the pin.

An elongated lance 114 is provided with its forward end 116 mounted in a cylindrical pin 117 which is mounted for rotational movement in a second opening 118 through the actuating lever above and slightly forward of the opening 111. The lance, which has a point 120 on its rearward-facing end, extends from the actuating lever 110 through an opening 122 in the injector assembly body 34. A cylindrical plug 123 is mounted on the lance 114 and moves within a cylindrical cavity 125 which extends from the opening 122 in the injector body 34. An elongated groove 114a is in a portion of the top surface of the lance 114 along its length. The groove provides a pathway for venting gas through a vent slot 127, which extends through the front facing surface 34a of the body 34 in the slot 107, into the top of the cavity 125, to the atmosphere. The lance point 120 is spaced apart from and adjacent the gas cylinder seal 56 when the actuating lever is in its unactuated position, as shown in FIG. 1, and the rearmost portion of the groove 114a is in the cavity 125.

The actuating lever 110 can be moved from its unactuated to its actuated position by squeezing it so that the front end 110a of the lever 110 moves upwardly toward the slot 107, while the back end pivots on the pin 112. As the lever moves to its actuated position, the lance is moved rearwardly through the opening 122, and the point 120 is forced through the frangible gas cylinder seal 56, puncturing the seal and releasing the gas from the cylinder. As the lance moves rearwardly, the plug 123 moves further into the cavity 125. The clearance between the lance 114 and the opening 122 is such that gas is prohibited from escaping in sufficient quantities to affect the operation of the injection device. As is described below in greater detail, after the gas has been released from the cylinder, and during the last portion of the movement of the actuating lever, the groove 114a extends into the passageway 66. Gas from behind the piston 40 (including gas in the passageway 66 and any gas remaining in the container 12) is then vented through the groove 114a, into the cavity 125, and out to the atmosphere through the vent 127. After the gas is vented to the atmosphere, the spring 42 returns the piston to its unactuated position at the back end 38 of the barrel.

The actuating lever is biased to its unactuated position by means of a leaf spring 124 mounted in the front portion 110a of the lever 110. The spring 124 extends upwardly from the lever 110 so that its curved upper end 126 contacts a surface 128 of the body 34 that extends horizontally below and defines the bottom wall of the passageway 72 and the top of the slot 107.

Figure 4:
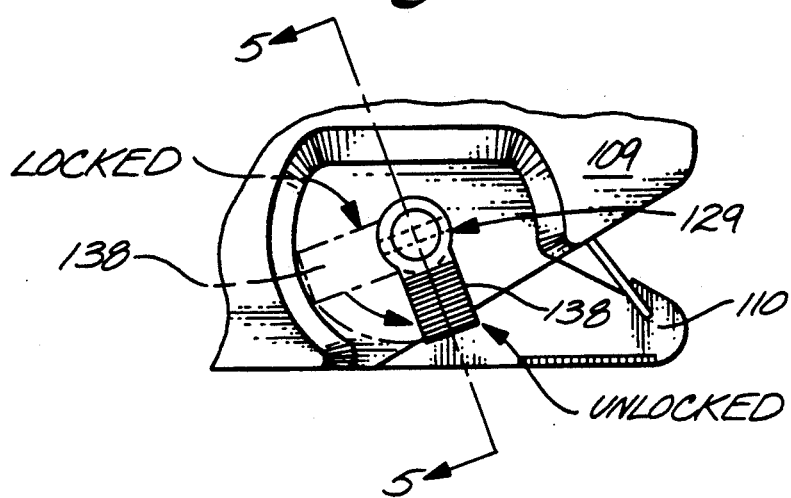
FIG. 4 is a semi-schematic, broken-away side view of FIG. 1 showing a safety device for locking the injection device actuating lever.
Figure 5:
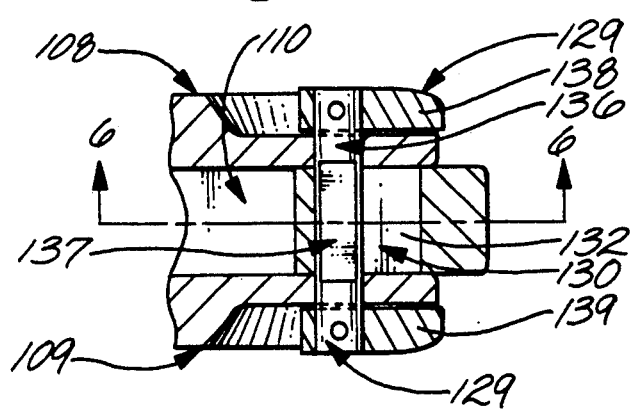
FIG. 5 is a semi-schematic, fragmentary, cross-sectional view taken on line 5—5 of FIG. 4.
Figure 6:
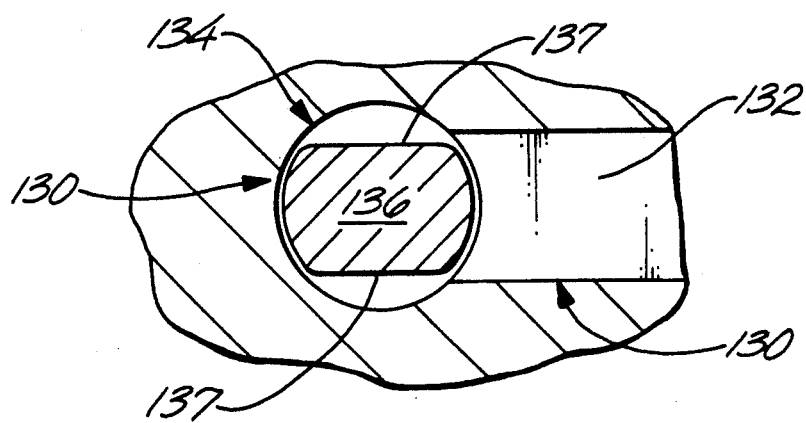
FIG. 6 is a semi-schematic, fragmentary, enlarged view taken on line 6—6 of FIG. 5.

Referring to FIGS. 4-6 (in addition to FIG. 1), a safety interlock 129 is shown which prohibits movement of the actuating lever 110 from its unactuated to its actuated position when the interlock is in the "locked" position. In a preferred embodiment, the interlock is provided by means of a keyhole-shaped slot 130 (best seen in FIGS. 1, 5 and 6) cut through the lever 110 in a portion of the lever forward of the openings 111 and 118. The slot has a narrow bottom portion 132 and a circular top portion 134. A lock rod 136, having flats 137 on opposite sides, is mounted on the injector body between the walls 108 and 109. The lock rod 136 can be rotated about an axis transverse to the length of the injector body by means of levers 138 and 139, each of which is in one end of the lock rod. The lock rod 136 extends through the circular top or enlarged portion 134 of the slot 130 when the actuating lever 110 is in its unactuated position (as shown in FIG. 1). When the rod 136 is in its first or locked position, the flats 137 extend across the slot as shown in FIG. 1, and the lever is prohibited from being moved upwardly, i.e., the lever is prohibited from being squeezed to its actuated position. Actuation of the lever is prohibited because the rod has a diameter greater than the width of the bottom portion 132 of the slot 130. When the levers 138 and 139 are moved in the direction of the arrow shown in FIG. 4, the safety moves from its locked to its unlocked position, with the flats 137 aligned along the length of the slot 130. The width of the rod between the flats is less than the width of the narrower portion 132 of the slot 130. Thus, when the rod 136 is in the unlocked position, it can move within the slot, enabling the actuating lever 110 to be moved upwardly into the slot 107, to its actuated position, as is shown in FIG. 14.

In a preferred embodiment of the needleless hypodermic injection device 10 provided in accordance with practice of principles of this invention, means are provided for varying the force of gas acting on the piston 40 to thereby vary the velocity of the medication as it is ejected through the ampule assembly orifice 22. Referring to FIGS. 7, 8 and 9, a first exemplary embodiment of a force-varying means provided in accordance with this invention comprises a gas-flow-regulator assembly 140 mounted at the back end 38 of the barrel 35 in place of the plug 51 described with reference to FIGS. 1 and 2. The flow-regulator assembly 140 comprises a body portion 142 that has a threaded end 144 for engaging the threads 53 in the opening 54 through the back end of the injector body 34. A groove 145 is around the circumference of the base of the threaded end 144 of the body 142. A disk 146, in the form of an open cylinder or cup having a flat center portion 148 with a circular wall 150 around its periphery and extending rearwardly, is mounted in the body 142. The disk 146 has an opening 152 through its center which is mounted on a hollow circular extension portion 154 of the body 142. The extension 154 acts like an axle on which the disk can be rotated.

A circular plenum piece 156 fits into the rearward-facing cylindrical cavity 158 formed by disk wall 150. The plenum piece 156 has a rearward-facing central cavity 160 which, in the illustrated embodiment, is circular, and an hexagonal opening 161 is through the center of the cavity 160. The opening 161 is mounted onto a further hollow extension 162 that is hexagonal in shape, is smaller in diameter, and extends from the hollow extension 154. A gas deflector plug 163, having a circular head 164 and a circular stem 167, is press fit into the cavity 160 of the plenum piece 164, with the stem 167 extending into the hollow extension 162. A cap 168, having threads 169 around its outer circumference, with an interior center portion 170 configured to engage the circular top portion 166 of the plug 163, is threaded into engagement with threads 171 on the rearward-facing end of the flow regulator body 142. The cap 168, when screwed in place, holds the flow-regulator assembly together.

In the illustrated embodiment, there are three sets of gas-flow-restricting orifices 172 spaced around the perimeter of the flat center portion 148 of the disk 146. Each orifice set includes five orifices, beginning with the largest in diameter designated 172a and decreasing in size in a counterclockwise direction, as shown in FIG. 5, to the smallest in diameter designated 172e. In one exemplary embodiment, the orifice 172a is 0.080 inch in diameter, the orifice 172b is 0.060 inch, the orifice 172c is 0.040 inch, the orifice 172d is 0.020 inch, and the orifice 172e is 0.010 inch. Other sized gas-flow-restricting orifices can be provided, if desired. Each orifice set is identical to the other set, and each orifice 172 is spaced apart 120° from each other orifice of the same size. The plenum piece 156 includes three outlets 174, 176 and 178 through it, spaced apart 120° from each other, each of which is in communication with a bore 180 through the center of the body 142. The bore 180 opens into the groove 145 which, in turn, is open to the gas flow passageway 66. Each of the plenum outlets 174, 176 and 178 directs gas released from the gas cylinder through one of the orifices 172 in each set of orifices and through one of three gas ports 182 spaced apart 120° from each other through the flow regulator body 142. Thus, gas released from the cylinder 12 passes through the passageway 66, into the groove 145 in the body 142, through the bore 180, and into the plenum piece 156. From the plenum piece 156, the gas passes through the outlets 174, 176 and 178, through three orifices 172, through the three associated gas ports 182, and into the cavity 70 to act on the rearward-facing surface 46 of the piston 40.

A handle 184 is mounted in the circular disk wall 150 and extends upwardly out through a slot 186 in the top portion of the regulator body 142. The handle 184 provides a means to rotate the disk 146 to a selected position for placing one orifice 172 in each of the three sets of orifices in alignment with one of the plenum outlets 174, 176 and 178. Thus, in the exemplary embodiment, the disk can be rotated through one of five positions where, in each such position, one of the gas-flow-restricting orifices of equal size in each set is in alignment with a different one of the plenum outlets. Numbers (not shown) can be positioned on the rear-facing surface 142a of the body 142 to line up with the handle 184 when the handle is in position corresponding to the particular size orifice aligned with the outlets 174, 176 and 178. In the illustrated embodiment, numbers 1–5 are on the surface 142a to provide five pressure settings.

Disks having more or fewer than three sets of orifices and having more or fewer than five orifices per set can be provided, if desired. There can be more or fewer than three outlets provided in the plenum pieces. The number of gas ports 182 corresponds to the number of plenum outlets which, in turn, corresponds to the number of sets of disk orifices 172.

A second preferred embodiment of a gas-flow-regulator assembly 186 for varying the force of gas acting on the piston 40 is shown in FIGS. 10–13. The flow-regulator assembly 186, having a body portion 187, is mounted at the back end 38 of the barrel 35 in place of the plug 51 described with reference to FIGS. 1 and 2. The assembly body 187 has a threaded end 188 for engaging the threads 53 in the opening 54 through the back end of the injector body 34. A groove 189, which is around the circumference of the base of the threaded end 188 of the body 187, is open to the passageway 66 in the injector body 34. The assembly 186 includes a valve seat 190 at the outlet end of a bore 191, which opens into the groove 189. A resilient ball 194 is downstream from the seat 190 for contacting the seat. A coil spring 196 is provided for adjustably biasing the ball onto the seat. If desired, a plug, or the like, can be used in place of the ball 194. The spring 196 is in an outlet chamber 197 between the ball 184 and the stem 198 of an adjustable knob 199, which is threaded into a horizontal opening 200 through the center of the end of the body 187 of the flow-regulator assembly 186. Three gas ports 202, 204 and 206, respectively, spaced apart 120° from each other, extend out from the chamber 197 through bores 208. In the illustrated embodiment, gas from the cylinder 12 passes through the passageway 66, into the groove 189, and through the bore 191. From the bore 191, the gas travels between the ball 194 and the seat 190, through the bores 208, and then through the three gas ports 202, 204 and 206 and into the cavity 70 to contact the rearwardly-facing surface 46 of the piston 40.

The knob 199 has a slot 212 through it extending around approximately the bottom one-third of its perimeter. An indicator pin 214 extends in a rearward direction out from the regulator assembly body 187 into the slot 212. When the knob 199 is turned in one direction, the stem 198 moves toward the ball 194, which increases the compression of the spring 196 holding the ball. An increase in the compression of the spring increases the force acting on the ball, holding it in engagement with the seat 190. When the knob 199 is turned in the opposite direction, the stem moves away from the ball, which decreases the compression on the spring 196 to thereby reduce the force holding the ball on the seat.

When the force holding the ball on the seat is increased, flow of gas is relatively more restricted as it passes between the ball and the seat 190. This increase in gas flow restriction results in less force being applied to the piston 40 by reducing the pressure on the piston. Providing less force on the piston reduces piston velocity/pressure, which results in a decrease in the velocity of the medication ejected through the orifice 22. Conversely, when the force holding the ball on the seat is decreased, the flow of gas between the ball and seat is increased, thereby increasing the force on the piston 40, resulting in an increase in the velocity of the medication ejected through the orifice 22. In one exemplary embodiment, the knob 199 has a series of numerals, or settings, from 1 to 5 on it, indicating the force being exerted. If desired, a cap 215 can be provided to cover the knob 199.

OPERATION

The operation of the components of the system provided in accordance with this invention can be understood by referring to FIGS. 13, 13A, and 14. FIG. 13 shows one embodiment of a method for filling the ampule assembly 14 with liquid medication. In this embodiment, the ampule assembly 14 is mounted onto a preferred embodiment of an adaptor assembly 220 provided in accordance with this invention, which, in turn, is snap mounted onto vial(s) 222 of liquid medication.

The adaptor assembly 220 of this invention includes an assembly body 224 made, for example, of a clear plastic. Other suitable materials can be used, if desired. The body 224 includes two cavities 226 and 228, respectively, spaced apart from each other on opposite ends of the body. The first cavity 226 is configured to receive the cap 230 on the vial 222 of liquid medication. The second cavity 228 has threads 230 for engaging threads 232 on the discharge or orifice end 23 of the ampule assembly 14. Preferably, the threads 230 and 232 are quick release threads, similar to the threads 25 and 39 on the end 24 of the ampule assembly and in the front end of the barrel, so that the ampule assembly can be mounted and removed from the cavity 228 by turning the assembly approximately one-half turn. Adaptor assemblies having first cavities of various sizes can be provided to accommodate the various sized caps of standard medication vials.

A diaphragm 234, made of flexible plastic or rubber, or the like, is mounted in the bottom of the cavity 228. As can be seen best in FIG. 13A, the diaphragm 234 has a cylindrical recess 235 formed in a portion of its center adjacent the cavity 228. The diaphragm has an elongated slit 236 extending through its center, registered with the cylindrical recess 235. It is contemplated that such a slit 236 will have a length of from about 0.030 inch to about 0.050 inch. Slits having other lengths can also be provided, if desired. The slit 236 is closed when the ampule assembly is not in the cavity and the diaphragm is in its non-flexed or original state (as is shown in FIG. 13A). When the ampule assembly is mounted in the cavity 228 (as is shown in FIG. 13), the end 23 of the assembly realigns the center portion of the diaphragm 234 to thereby open the slit 236 into the recess 235. When the ampule assembly is removed, the diaphragm returns to its original state and the slit 236 returns to its original closed position. The diaphragm 234 provides an air-restricting seal between the end 23 of the ampule assembly 14 and the adaptor assembly 220 when the ampule assembly is mounted therein. If desired, a hole can be used instead of a slit.

A hollow, tubular needle 237 is mounted in the adaptor assembly body 224. The needle is through the center of the portion 238 of the body 224 that separates the first and second cavities 226 and 228 from each other. The top opening of the needle is positioned in the cylindrical diaphragm recess 235 with its point extending a sufficient distance into the first adaptor body cavity 226 to pierce the cap 230 of the vial 222 when the adaptor assembly is on the vial. A cap 239 can be provided for insertion into the cavity 228 to maintain sterility when the ampule is not in the cavity 228 for filling. In the illustrated embodiment, the cap 239 is attached to the adaptor body 224 by means of a "living" hinge 241.

To provide for filling the ampule assembly 14, a vial 222 filled with liquid medication is snapped into the cavity 226 of the adaptor assembly 220 so that the needle 237 is through the cap 230 on the vial. A disposable ampule assembly is then taken from its sterile container and the cap 239 is then removed from the adaptor cavity 228. The ampule assembly 14, with the plunger assembly 26 partially inserted into the ampule cavity 20, is then screwed into the adaptor body cavity 228, so that the ampule threads 232 engage the threads 230 in the cavity 228. As is illustrated in FIG. 13, mounting of the ampule assembly in the cavity 228 forces open the slit 236 in the diaphragm 234. The adaptor assembly 224 and the vial 222 are then inverted so that liquid medication in the vial covers the point of the needle 237. Air is then pumped into the vial 222 by pushing the plunger assembly 26 forward in the direction of the arrow marked "A" in FIG. 13. Medication is then drawn in through the needle 237, into the cylindrical diaphragm recess 235, through the open diaphragm slit 236, through the ampule assembly orifice 22, and into the ampule cavity 20 by pulling on the end 33 of the plunger assembly 26 to move the plunger assembly in the direction of the arrow marked "B" in FIG. 13.

After the medication fills the cavity 20 to the appropriate level, as indicated by the position of the flange 31 of the piston 27 relative to the graduations 29 on the ampule body 18 (shown in FIG. 1), the ampule assembly 14 is unscrewed from the filling assembly cavity 228, and the cap 239 reinstalled. Preferably, the ampule assembly 14 is filled with slightly more medication than is desired so that any air in the ampule can be ejected by pushing the plunger 26 back into the cavity 20 an appropriate distance, while the ampule assembly is held in the vertical position, with the orifice 22 up.

The design and configuration of the adaptor assembly diaphragm is an important feature of the system provided in accordance with practice of principles of this invention. As is mentioned previously, when the end 23 of the ampule assembly is mounted in the cavity 228, a liquid-tight seal is provided between the end 23 and the diaphragm 234. After the ampule assembly is filled with liquid medication, and as it is being removed from the cavity 228, the diaphragm returns to its original condition, as shown in FIG. 13A, thereby closing the slit 236 and preventing liquid medication from passing from the vial into the cavity 228. Thus, the cavity 228 remains dry and free of medication. This ensures that residual medication, which could become contaminated, will not be in the adaptor cavity 228 between fillings.

In order to enable a person who presently uses standard skin-penetration syringes to easily adapt to using the injection device 10 of the present invention, it is preferred that the cavity 20 of the ampule assembly 14 have substantially the same circular cross-section as standard syringes so that a given longitudinal movement of the plunger assembly 26 in the present invention will draw substantially the same volume of liquid medication into the cavity 20 as would be drawn into a conventional syringe by the same amount of movement. Thus, an insulin-dependent diabetic or other long-term medication user, or health care professional, who has become accustomed to filling a standard syringe for injecting medication, will be able to use the same learned movement to fill the ampule of the present invention.

Turning now to FIG. 14, after the above-described filling operation of the cavity 20 of the ampule assembly 14 has been completed, the end 24 of the ampule assembly 14 is screwed into the threaded forward end 36 of the barrel 35 of the injector assembly 16. As was described above with reference to FIG. 1, as the ampule assembly is screwed into the barrel 35, the special quick release ampule assembly threads 25 engage the portion 78 of the valve stem 74 and push the valve stem rearwardly toward the valve seat 82. When the ampule assembly is fully mounted, i.e., when its end 24 has been screwed tightly into the barrel 35 (as shown in FIG. 14), it holds the valve stem 74 in place at its rearmost position in the passageway 72 to thereby hold or trap the ball 84 in sealing engagement on the valve seat 82. When the ball 84 is held on the seat 82 by the valve stem 74, gas cannot vent to the atmosphere through the passageway 72.

If desired, disposable ampule assemblies can be provided pre-filled with the appropriate medication. In this embodiment, no filling operation is necessary, and the ampule assembly can be removed from its sterile package and mounted directly onto the injector assembly.

Prior to externally mounting the ampule assembly 14 onto the injector assembly 16, and with the safety 129 in the locked position, the chamber 55 is opened by removing the plug 61, and a fresh $CO_2$ container 12 is installed. The plug is then replaced to thereby hold the container 12 securely in the chamber.

After the injector assembly 16 is prepared as described above, with the ampule assembly 14 and $CO_2$ container 12 loaded, the end 23 of the ampule assembly 14 is placed against the properly prepared skin 240 of the user. At this time, the safety lock rod 136 is rotated by means of the levers 138 and 139 from its locked position with the flats 137 across the slot 130, as shown in FIG. 1, to its unlocked position with the flats 137 lined up with the slot, as shown in FIG. 14. When the safety is unlocked, the narrow portion 132 of the slot 130 can be moved by the rod. After moving the safety to its unlocked position, the actuating lever 110 is squeezed to move it upwardly into the slot 107 in the assembly body 34 toward the barrel 35.

As the actuating lever moves toward its actuated position (as shown in FIG. 14), the lance 114 is moved rearwardly through the opening 122 toward the container 12, and the plug 123 moves further into the cavity 125. The lance point 120 is forced through the frangible container seal 56, puncturing the seal and releasing the compressed gas from the container. The released gas travels through the outlet 68 and is conducted via the passageway 66, into the groove 57 in the plug 51, through the bore 58 and into the cavity 70, to act on the rearward-facing surface 46 of the piston 40. The force of the gas drives the piston 40 forward against the spring 42 toward the forward end 36 of the barrel 35. The piston strikes the head 33 of the plunger 26, engaging the plunger and forcing it forward against the liquid medication contained in the cavity 20 of the ampule 14. Preferably, the face of the piston is concave so that when the piston engages the plunger head 33, the concave face aligns the plunger in the center of the barrel 35 and maintains the proper plunger alignment as the plunger moves forward. As the plunger moves forward, liquid medication is ejected through the orifice 22 of the ampule 14 and into the skin 240. The use of the injection device 10 of the present invention leaves no puncture wound and causes little pain to the user.

The force of the gas acting on the rearward-facing surface 46 of the piston 40 is directly proportional both to the pressure of the gas and to the area of the surface 46. Thus, when a piston (and associated barrel) with a relatively larger cross-sectional area is used, the force on the rearward-facing surface 46 exerted by the gas at a given pressure will be relatively larger. When a piston (and associated barrel) with a relatively smaller cross-sectional area is used, the force on the rearward-facing surface will be relatively smaller. The piston and barrel can be considered to act in combination as an accumulator for magnifying the force provided by the compressed gas.

After the liquid medication has been injected into the patient's tissues as described above, the actuating lever 110 is released. The actuating lever returns to its unactuated position (as shown in FIG. 1) by the action of the spring 124. The lock rod 136 of the safety 129 is rotated to its locked position by moving the levers 138 and 139 so that the flats 137 are across the slot 130, as shown in FIG. 1.

As the piston moves forward during operation, air pressure in the barrel 35, downstream from the piston, vents out through the vent 244, which extends through the bottom of the barrel 35 into the passageway 72, through the slot 87, to the atmosphere. As the actuating lever is moved past the point at which the gas container seal 56 is punctured, the groove 114a in the top surface of the lance moves into the passageway 66. Gas pressure in the barrel behind the piston 40 (and the gas in the passageway 66 and in the container 12) is then vented through the groove 114a into the cavity 125 and out through the vent slot 127 to the atmosphere. Venting gas to the atmosphere through the slot 127 is completed almost instantaneously, so that the actuating lever can be released quickly from its fully-actuated position. (Other arrangements for venting the gas pressure behind the piston 40 to the atmosphere can be used, if desired.) When the pressure behind the piston is vented sufficiently through the slot 127 to provide less force on the rearward-facing surface 46 of the piston 40 than the force provided by the spring 42, the piston is pushed by the spring back to its unactuated position at the back end 38 of the barrel.

The injection device 10 can be prepared to be actuated again by removing the plug 61, replacing the spent gas container 12 in the chamber 55 with a fresh container, and reinstalling the plug 61. After this operation is complete, a fresh ampule assembly can be removed from its sterile container and filled with liquid medication for use as described above.

Turning to FIGS. 7-10 (in addition to FIG. 14) the operation of the injection device lo, when the gas-flow-regulator assembly 140 is mounted in the back end 38 of the barrel 35 in place of the plug 51, is described. The preparation of the device 10 for the hypodermic injection is the same as the preparation described above with reference to FIG. 14. In addition, however, when the device 10 has the flow-regulator assembly 140 installed, a determination is made by the user regarding the desired velocity of medication ejected through the orifice 22. This evaluation can be done by correlating the medication viscosity with desired orifice size and desired injection velocity and selecting the appropriately sized disk orifice. For example, when a disk such as the one described with reference to FIGS. 7-10 is used, having three orifice sets with five orifices in each set, a determination is made as to which orifice setting will provide the appropriate minimum medication injection velocity to penetrate the skin as required. Once the desired orifice setting is determined, the disk is rotated by means of the handle 84 to the proper setting from 1 to 5 to thereby align the orifices 172 of the selected size with the plenum outlets 174, 176 and 178.

After the disk setting is complete, the end 23 of the ampule assembly is placed against the properly prepared skin 240 (as shown in FIG. 14), the safety 129 is unlocked, and the lever 110 is actuated by squeezing, thereby releasing the gas from the compressed gas container 12. The gas passes from the container through the opening 68 and into the passageway 66. From the passageway 66, it passes into the circumferential groove 145 and through the assembly body bore 180. From the bore 180, the gas passes through the plenum outlets 174, 176 and 178, through the three selected disk orifices 172 lined up with the associated plenum outlets, and through the three gas ports 182 into the cavity 70 behind the piston 40. The gas entering the cavity 70 acts on the rearward-facing surface 46 of the piston 40 to drive it forward to thereby eject the medication through the orifice 22 of the ampule assembly 14.

Depending on the disk orifice size selected by the user, the gas flow to the piston 40 is more or less restricted, thereby enabling the user to select the minimum injection velocity (as provided by the particular orifice sizes in the disk) sufficient for injecting the liquid medication through the skin at the injection location. Thus, for example, if a relatively smaller hole size is selected, gas flow is relatively more restricted, thereby reducing the pressure of gas acting on the piston and reducing the force on the piston. The restricted gas flow causes the piston 40 to move more slowly toward the front end 36 of the barrel 35, thus providing liquid medication having relatively less injection velocity.

Figure 10:
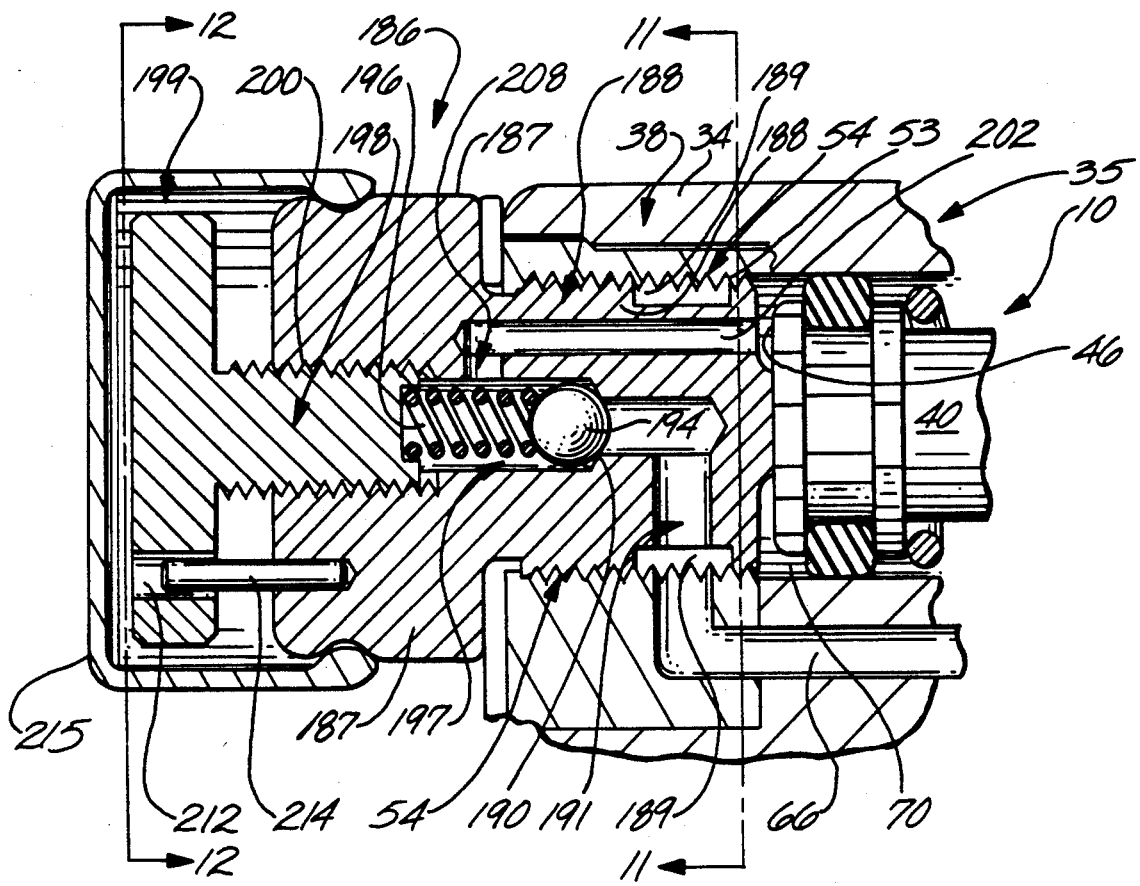
FIG. 10 is a semi-schematic, fragmentary, cross-sectional side view of the needleless hypodermic device of FIG. 1, having mounted thereon a second embodiment of a gas-flow-regulator assembly provided in accordance with this invention.
Figure 11:
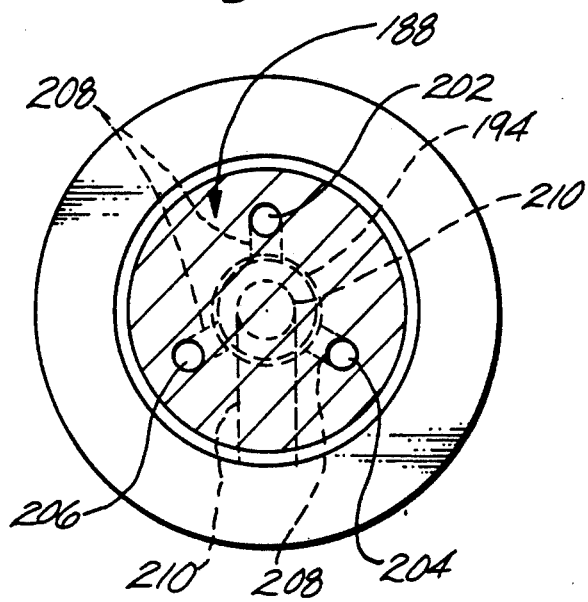
FIG. 11 is a semi-schematic, cross-sectional view of the gas-flow-regulator assembly taken on line 11—11 of FIG. 10.
Figure 12:
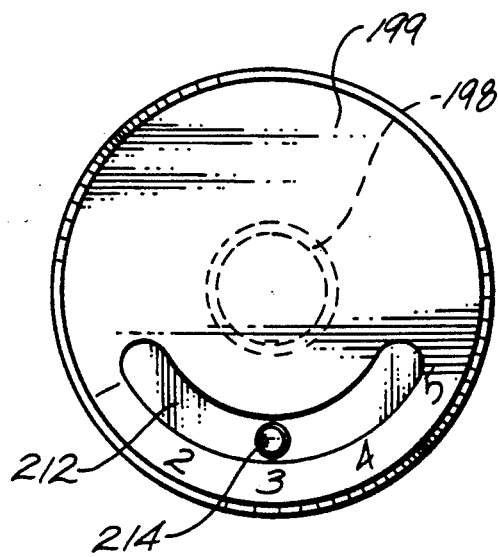
FIG. 12 is a semi-schematic view of the gas-flow-regulator assembly taken in line 12—12 of FIG. 10 showing an adjustment knob.

Turning to FIGS. 10-12 (in addition to FIG. 14), the operation of the injection device 10, when the gas-flow-regulator assembly 186 is mounted in the back end 38 of the barrel 35, is described.

The preparation of the device 10 for hypodermic injection is the same as the preparation described above with reference to FIG. 14. In addition, however, when the device 10 has the flow-regulator assembly 186 installed, a determination is made by the user regarding the desired velocity of medication to be ejected through the orifice 22. This evaluation is the same as the evaluation made when the device 10 has the flow-regulator assembly 140 mounted thereon as is described above.

Although there are an infinite number of positions to which the knob 199 on the assembly 186 can be turned for providing more or less tension on the regulator assembly spring 196, in the exemplary embodiment, there are five numbered positions or settings. For example, when the knob is turned to the position No. 5, maximum force is on the assembly spring, thereby minimizing the amount of gas that will pass between the ball 194 and the seat 190 during a given time period, to thereby relatively decrease the pressure of gas behind the piston 40. Decreasing the pressure of gas behind the piston decreases the force of the gas acting on the rearward-facing surface 46 of the piston, thereby decreasing piston velocity. This, in turn, decreases the velocity of the medication as it is being ejected through the orifice 22 in the ampule assembly. Conversely, when the knob is turned to the position No. 1, the force on the spring is reduced, thereby allowing relatively more gas to pass between the seat 190 and the ball 194 during a given time period, to increase the pressure of gas behind the piston 40. Increasing the pressure of gas behind the piston increases the force on the rearward-facing surface 46 of the piston, thereby increasing piston velocity. The increase in piston velocity increases the velocity of the medication being ejected through the orifice 22.

After the knob 199 is set to its desired position, the end 23 of the ampule assembly is placed against the properly prepared skin 240, the safety 129 is unlocked, and the lever 110 is actuated, releasing the gas from the compressed gas container 12. The gas passes from the container, through the opening 68, and into the passageway 66. From the passageway 66, it passes into the circumferential groove 189, into the assembly body bore 191, past the seat 190 and ball 194, into the cavity 197. The gas exits the cavity 197 through the bores 208, through the gas ports 202, 204 and 206, and into the cavity 70 behind the piston 40. The gas entering the cavity 70 acts on the rearward-facing surface 46 of the piston 40 to drive it forward to thereby eject the medication through the orifice 22 of the ampule assembly 14.

The setting on the knob 199 controls the velocity of the medication being ejected through the orifice 22.

The embodiments of the injection device 10, having either the flow-regulator assembly 140 or the flow-regulator assembly 186, provide an easy and efficient means to select the minimum required velocity to appropriately penetrate the skin of the user for a given injection site and liquid medication viscosity. Furthermore, providing an injection device of simple construction enables the device to be manufactured economically and enhances reliability.

The above descriptions of preferred embodiments of the hypodermic injection system of this invention, which comprises the needleless hypodermic device 10, which includes an injector assembly 16 having an injector body 34 with a chamber 55 for a compressed gas container 12 and an ampule assembly 14 mounted on the injector body, and the adaptor assembly 220, are for illustrative purposes. Because of variations which will be apparent to those skilled in the art, the present invention is not intended to be limited to the particular embodiments described above. The scope of the invention is defined in the following claims.

What is claimed is:

1. A gas-pressure-actuated needleless hypodermic device for injecting liquid medication through the skin of persons or animals, the device comprising:
   (a) an ampule assembly comprising:
      (i) a body having a cavity for holding liquid medication between first and second ends of the body;
      (ii) an orifice in the first end of the body through which such liquid medication can flow into and out from the cavity; and
      (iii) a plunger assembly movable within the cavity for drawing the liquid medication into the cavity and for forcing the liquid medication out from the cavity;
   (b) an injector assembly for receiving and mounting the ampule assembly and for providing a force to move the plunger assembly to thereby force the liquid medication through the ampule assembly orifice, the injector assembly comprising:
      (i) an injector body including a barrel closed at its back end, wherein the front end of the barrel is open and configured to receive the second end of the ampule assembly body to thereby mount the ampule assembly on the barrel;
      (ii) a piston mounted for sliding movement in the barrel, the piston configured to be pushed by gas pressure from an at-rest position at the back end of the barrel toward the front end of the barrel;

(iii) a chamber in the injector body configured to house a compressed gas container;

(iv) a first passageway in the injector body through which gas flows from the gas container in the gas container chamber to the barrel to provide a force on the rearward-facing surface of the piston to move the piston toward the front end of the barrel;

(v) a second passageway in the injector body configured to be open for venting gas released from the gas container to the atmosphere when the end of the ampule assembly is not mounted in the injector assembly barrel;

(vi) means for sealing the second passageway to prevent venting gas through the passageway to the atmosphere, the seal provided only when the ampule assembly is mounted in the injector assembly barrel; and (vii) means for releasing gas from the gas container to provide the force on the rearward-facing surface of the piston to thereby move the piston toward the front end of the barrel and into contact with the plunger assembly and for moving the plunger assembly toward the orifice to thereby eject the liquid medication from the cavity out through the orifice.

2. A needleless hypodermic injection device as is claimed in claim 1 wherein the second passageway sealing means comprise:

(a) a valve stem mounted in the second passageway for sliding movement along the length of the second passageway, the valve stem being an L-shaped rod with the forward end of the valve stem having a bend extending upwardly into the opening in the front end of the injector body barrel;

(b) a valve seat at the upstream end of the second passageway; and (c) a ball located between the valve seat and the back end of the valve stem, wherein the front end of the valve stem engages the second end of the ampule assembly body as the ampule assembly body is being mounted in the barrel so that the valve stem is moved by the ampule assembly body toward the valve seat during the mounting operation, the ampule assembly holding the valve stem in place at its rearmost position when the ampule assembly end is fully mounted in the barrel to thereby trap the ball in gas-sealing engagement on the valve seat.

3. A needleless hypodermic injection device as is claimed in claim 1 wherein the gas-releasing means comprise:

(a) a actuating lever mounted on the injector body; and (b) an elongated lance having one end mounted on the actuating lever and having a point on its opposite end, the lance extending through an opening in the injector body so that:

(i) the lance point is spaced apart from and is adjacent a frangible seal on a compressed gas container positioned in the gas container chamber when the actuating lever is in its unactuated position; and (ii) the lance point is movable to a position by which it punctures the gas container seal to thereby release the gas from the container when the actuating lever is moved to its actuated position.

4. A needleless hypodermic injection device as is claimed in claim 1 which also comprises means for varying the force of the gas acting on the piston to thereby vary the velocity of the medication as it is ejected through the ampule assembly orifice.

5. A needleless hypodermic injection device as is claimed in claim 4 wherein the force-varying means comprise a gas-flow-regulator assembly comprising a disk having a plurality of gas-flow-restricting orifices of different sizes therethrough mounted in the injector body, the location of the disk being such that gas released from a gas container housed in the gas container chamber must pass through at least one such gas-flow-restricting orifice prior to contacting the piston, the flow-restricting orifices configured to be selectively positioned in the gas flow path by rotating the disk.

6. A needleless hypodermic injection device as is claimed in claim 5 wherein the disk has three sets of gas-flow-restricting orifices spaced around the perimeter, with each such orifice set being identical and each orifice being spaced apart 120° from each other orifice of the same size, the disk configured to be rotated so that in each selected position three orifices of equal size are in the gas flow path between the gas container and the piston.

7. A needleless hypodermic injection device as is claimed in claim 4 wherein the force-varying means comprise a gas-flow-regulator assembly that comprises a throttle valve having a valve seat in the gas flow path between a gas container housed in the gas container chamber and the piston, sealing means for engagement with the valve seat, a spring for biasing the sealing means on the seat, and means for varying the compression of the spring to provide a variable force for holding the sealing means on the seat.

8. A needleless hypodermic injection device as is claimed in claim 7 wherein the sealing means is a ball.

9. A needleless hypodermic injection device as is claimed in claim 1 wherein the plunger assembly has a piston on its end which moves within the ampule cavity, the piston having a groove around the circumference of its front end so that a flange is at the front-facing surface of the piston.

10. A gas-actuated needleless hypodermic device for injecting liquid medication through the skin of persons or animals, the device comprising:

(a) an ampule assembly comprising:

(i) a body having a cavity for holding liquid medication between first and second ends of the body;

(ii) an orifice in the first end of the body through which such liquid medication can flow into and out from the cavity; and (iii) a plunger assembly movable within the cavity for drawing the liquid medication into the cavity and for forcing the liquid medication out from the cavity;

(b) an injector assembly for receiving and mounting the ampule assembly and for providing a force to move the plunger assembly to thereby force the liquid medication through the ampule assembly orifice, the injector assembly comprising:

(i) an injector body including a barrel closed at its back end, wherein the front end of the barrel is open and configured to receive the second end of the ampule assembly body to thereby mount the ampule assembly on the barrel;

(ii) a piston mounted for sliding movement in the barrel, the piston pushed by gas pressure from an at-rest position at the back end of the barrel toward the front end of the barrel;

(iii) a chamber in the injector body configured to house a compressed gas container;

(iv) a passageway in the injector body through which gas flows from a gas container in the gas container chamber to the barrel to provide a force on the rearward-facing surface of the piston to move the piston toward the front end of the barrel;

(v) means for venting gas released from the gas container to the atmosphere when the ampule assembly end is not fully mounted in the injector assembly barrel so that the gas pressure in the injector assembly does not increase to a sufficient level to move the piston; and (vi) means for releasing gas from the gas container to provide the force on the rearward-facing surface of the piston to thereby move the piston toward the front end of the barrel and into contact with the ampule assembly plunger assembly for moving the plunger assembly toward the orifice to thereby eject the liquid medication out from the cavity through the orifice.

11. A needleless hypodermic injection device as is claimed in claim 10 wherein the gas-venting means comprise an opening through the injector body to the atmosphere.

12. A needleless hypodermic injection device as is claimed in claim 11 additionally comprising means for sealing the injector body opening to prevent release of gas to the atmosphere, the seal provided only when the second end of the ampule assembly is fully mounted in the injector assembly barrel, the sealing means comprising:

(a) a valve seat on the outlet end of the injector body opening;

(b) a slide mounted in the injector body for movement toward and away from the valve seat, a pin extending from the front end of the slide into the opening in the forward end of the injector body barrel;

(c) a ball located between the valve seat and the rear end of the slide; and (d) means on the ampule assembly to engage the pin as the assembly is being mounted in the front end of the barrel to move the slide toward the valve seat during the mounting operation and to hold the slide in place at its rearmost position when the ampule assembly second end is fully mounted in the barrel to thereby trap the ball in gas-sealing engagement on the valve seat.

13. A needleless hypodermic injection device as is claimed in claim 10 wherein the gas-releasing means comprise:

(a) an actuating lever mounted on the injector body; and (b) an elongated lance having one end mounted on the actuating lever and having a point on its opposite end, the lance extending through an opening in the injector body so that:

(i) the lance point is spaced apart from and is adjacent a frangible seal on a compressed gas container positioned in the gas container chamber when the actuating lever is in its unactuated position; and (ii) the lance point is movable to a position by which it punctures the gas container seal to thereby release the gas from the container when the actuating lever is moved to its actuated position.

14. A needleless hypodermic injection device as is claimed in claim 10 which also comprises means for varying the force of the gas acting on the piston to thereby vary the velocity of the medication as it is ejected through the ampule assembly orifice.

15. A needleless hypodermic injection device as is claimed in claim 14 wherein the force-varying means comprise a gas-flow-regulator assembly comprising a disk having a plurality of gas-flow-restricting orifices of different sizes therethrough mounted in the injector body, the location of the disk being such that gas released from a gas container housed in the gas container chamber must pass through at least one such gas-flow-restricting orifice prior to contacting the piston, the flow-restricting orifices configured to be selectively positioned in the gas flow path by rotating the disk.

16. A needleless hypodermic injection device as is claimed in claim 15 wherein the disk has three sets of gas-flow-restricting orifices spaced around the perimeter, with each such orifice set being identical and each orifice being spaced apart 120° from each other orifice of the same size, the disk configured to be rotated so that in each selected position three orifices of equal size are in the gas flow path between the gas container and the piston.

17. A needleless hypodermic injection device as is claimed in claim 14 wherein the force-varying means comprise a gas-flow-regulator assembly that comprises a throttle valve having a valve seat in the gas flow path between a gas container housed in the gas container chamber and the piston, sealing means for engagement with the valve seat, a spring for biasing the sealing means on the seat, and means for varying the compression of the spring to provide a variable force for holding the sealing means on the seat.

18. A needleless hypodermic injection device as is claimed in claim 17 wherein the sealing means is a ball.

19. A needleless hypodermic injection device as is claimed in claim 10 wherein the plunger assembly has a piston on its end which moves within the ampule cavity, the piston having a groove around the circumference of its front end so that a flange is at the front-facing surface of the piston.

20. A gas-pressure-actuated needleless hypodermic device for injecting liquid medication through the skin of persons or animals, the device comprising:

(a) an ampule assembly comprising:

(i) a body having a cavity for holding liquid medication between first and second ends of the body;

(ii) an orifice in the first end of the body through which such liquid medication can flow into and out from the cavity; and (iii) a plunger assembly movable within the cavity for drawing the liquid medication into the cavity and for forcing the liquid medication out from the cavity;

(b) an injector assembly for receiving and mounting the ampule assembly and for providing a force to move the plunger assembly to thereby force the liquid medication through the ampule assembly orifice, the injector assembly comprising:

(i) an injector body including a barrel closed at its back end, wherein the front end of the barrel is open and configured to receive the end of the ampule assembly body to thereby mount the ampule assembly on the barrel;

(ii) a piston mounted for sliding movement in the barrel, the piston configured to be pushed by gas pressure from an at-rest position at the back end of the barrel toward the front end of the barrel;

(iii) a chamber in the injector body configured to house a container containing compressed gas;

(iv) a gas container in the chamber having a frangible seal on its end;

(v) a first passageway in the injector body through which gas flows from the gas container to the barrel to provide a force on the rearward-facing surface of the piston to move the piston toward the front end of the barrel;

(vi) a second passageway in the injector body configured to be open for venting gas released from the gas container to the atmosphere when the end of the ampule assembly is not fully mounted in the injector assembly barrel;

(vii) means for sealing the second passageway to prevent venting gas through the passageway to the atmosphere, the seal provided only when the ampule assembly second end is fully mounted in the injector assembly barrel;

(viii) means for piercing the frangible gas container seal for releasing gas from the container to provide the force on the rearward-facing surface of the piston to thereby move the piston toward the front end of the barrel and into contact with the plunger assembly and for moving the plunger assembly toward the orifice to thereby eject the liquid medication out from the cavity through the orifice; and (ix) means for varying the force of the gas acting on the piston to thereby vary the velocity of the medication as it is ejected through the ampule assembly orifice.

21. A needleless hypodermic injection device as is claimed in claim 20 wherein the second passageway sealing means comprise:

(a) a valve stem mounted in the second passageway for sliding movement along the length of the second passageway, the valve stem being an L-shaped rod with the forward end of the valve stem having a bend extending into the opening in the front of the injector body barrel;

(b) a valve seat at the upstream end of the second passageway; and (c) a ball located between the valve seat and the back end of the valve stem, wherein the front end of the valve stem engages the second end of the ampule assembly body as the assembly is being mounted in the barrel so that the valve stem is moved toward the valve seat during the mounting operation, the ampule assembly holding the valve stem in place at its rearmost position when the ampule assembly is fully mounted in the barrel to thereby trap the ball in gas-sealing engagement on the valve seat.

22. A needleless hypodermic injection device as is claimed in claim 20 wherein the frangible gas-seal-piercing means comprise:

(a) an actuating lever mounted on the injector body; and (b) an elongated lance having one end mounted on the actuating lever and having a point on its opposite end, the lance extending through an opening in the injector body so that:

(i) the lance point is spaced apart from and is adjacent the frangible gas container seal when the actuating lever is in its unactuated position; and (ii) the lance point is movable to a position by which it punctures the frangible seal to thereby release the gas from the container when the actuating lever is moved to its actuated position.

23. A needleless hypodermic injection device as is claimed in claim 20 wherein the force-varying means comprise a gas-flow-regulator assembly comprising a disk having a plurality of gas-flow-restricting orifices of different sizes therethrough mounted in the injector body, the location of the disk being such that gas released from the container must pass through at least one such gas-flow-restricting orifice prior to contacting the piston, the flow-restricting orifices configured to be selectively positioned in the gas flow path by rotating the disk.

24. A needleless hypodermic injection device as is claimed in claim 23 wherein the disk has three sets of gas-flow-restricting orifices spaced around the perimeter, with each such orifice set being identical and each orifice being spaced apart 120° from each other orifice of the same size, the disk configured to be rotated so that in each selected position three orifices of equal size are in the gas flow path between the gas container and the piston.

25. A needleless hypodermic injection device as is claimed in claim 20 wherein the force-varying means comprise a gas-flow-regulator assembly that comprises a throttle valve having a valve seat in the gas flow path between the gas container and the piston, a ball for engagement with the valve seat, a spring for biasing the ball onto the seat, and means for varying the compression of the spring to provide a variable force to holding the ball on the seat.

26. A gas-pressure-actuated needleless hypodermic device for injecting liquid medication through the skin of persons or animals, the device comprising:

(a) an ampule assembly comprising:

(i) a body having a cavity for holding liquid medication between first and second ends of the body;

(ii) an orifice in the first end of the body through which such liquid medication can flow into and out from the cavity; and (iii) a plunger assembly movable within the cavity for drawing the liquid medication into the cavity and for forcing the liquid medication out from the cavity;

(b) an injector assembly for receiving and mounting the ampule assembly and for providing a force to move the plunger assembly to thereby force the liquid medication through the ampule assembly orifice, the injector assembly comprising:

(i) an injector body including a barrel closed at its back end, wherein the front end of the barrel is open and configured to receive the end of the ampule assembly to thereby mount the ampule assembly on the barrel;

(ii) a piston mounted for sliding movement in the barrel, the piston configured to be pushed by gas pressure from an at-rest position at the back end of the barrel toward the front end of the barrel;

(iii) a chamber in the injector body configured to house a container containing compressed gas;

(iv) a gas container in the chamber having a frangible seal on its end;

(v) a passageway in the injector body through which gas flows from the gas container to the barrel to provide a force on the rearward-facing surface of the piston to move the piston toward the front end of the barrel;

(vi) an opening through the injector body to the atmosphere for venting gas released from the gas container to the atmosphere when the ampule assembly end is not fully mounted in the injector assembly barrel;

(vii) means for sealing the injector body opening to prevent release of gas to the atmosphere, the seal provided only when the ampule assembly is fully mounted in the injector assembly barrel, the sealing means comprising:

(a) a valve seat on the outlet end of the injector body opening;

(b) a slide mounted in the injector body for movement toward and away from the valve seat, a pin extending from the front end of the slide into the opening in the forward end of the injector body barrel;

(c) a ball located between the valve seat and the rear end of the slide; and (d) means on the ampule assembly to engage the pin as the assembly is being mounted in the front end of the barrel to move the slide toward the valve seat during the mounting operation and to hold the slide in place at its rearmost position when the ampule assembly end is fully mounted in the barrel to thereby trap the ball in gas-sealing engagement on the valve seat;

(viii) means for piercing the frangible gas container seal for releasing gas from the container to provide the force on the rearward-facing surface of the piston to thereby move the piston toward the front end of the barrel and into contact with the plunger assembly and for moving the plunger assembly toward the orifice to thereby eject the liquid medication out from the cavity through the orifice; and (ix) means for varying the force of the gas acting on the piston to thereby vary the velocity of the medication as it is ejected through the ampule assembly orifice, the force-varying means comprising a gas-flow-regulator assembly that comprises a throttle valve having a valve seat in the gas flow path between the gas container and the piston, a ball for engagement with the valve seat, a spring for biasing the ball onto the seat, and means for varying the tension on the spring to provide a variable force for holding the ball on the seat.

27. A gas-pressure-actuated needleless hypodermic device for injecting liquid medication through the skin of persons or animals, the device comprising:

(a) an ampule assembly comprising:

(i) a body having a cavity for holding liquid medication between first and second ends of the body;

(ii) an orifice in the first end of the body through which such liquid medication can flow into and out from the cavity; and (iii) a plunger assembly movable within the cavity for drawing the liquid medication into the cavity and for forcing the liquid medication out from the cavity;

(b) an injector assembly for receiving and mounting the ampule assembly and for providing a force to move the plunger assembly to thereby force the liquid medication through the ampule assembly orifice, the injector assembly comprising:

(i) an injector body including a barrel closed at its back end, wherein the front end of the barrel is open and configured to receive the end of the ampule assembly to thereby mount the ampule assembly on the barrel;

(ii) a piston mounted for sliding movement in the barrel, the piston configured to be pushed by gas pressure from an at-rest position at the back end of the barrel toward the front end of the barrel;

(iii) a chamber in the injector body configured to house a container containing compressed gas;

(iv) a gas container in the chamber having a frangible seal on its end;

(v) a passageway in the injector body through which gas flows from the gas container to the barrel to provide a force on the rearward-facing surface of the piston to move the piston toward the front end of the barrel;

(vi) means for piercing the frangible gas container seal for releasing gas from the container to provide the force on the rearward-facing surface of the piston to thereby move the piston toward the front end of the barrel and into contact with the plunger assembly and for moving the plunger assembly toward the orifice to thereby eject the liquid medication out from the cavity through the orifice; and (vii) means for varying the force of the gas acting on the piston to thereby vary the velocity of the medication as it is ejected through the ampule assembly orifice, the force-varying means comprising a gas-flow-regulator assembly comprising a disk having a plurality of gas-flow-restricting orifices of different sizes therethrough mounted in the injector body, the location of the disk being such that gas released from the container must pass through at least one such gas-flow-restricting orifice prior to contacting the piston, the flow-restricting orifices configured to be selectively positioned in the gas flow path by rotating the disk.

28. A gas-pressure-actuated needleless hypodermic device for injecting liquid medication through the skin of persons or animals, the device comprising:

(a) an ampule assembly comprising:

(i) a body having a cavity for holding liquid medication between first and second ends of the body;

(ii) an orifice in the first end of the body through which such liquid medication can flow into and out from the cavity; and (iii) a plunger assembly movable within the cavity for drawing the liquid medication into the cavity and for forcing the liquid medication out from the cavity;

(b) an injector assembly for receiving and externally mounting the ampule assembly and for providing a force to move the plunger assembly to thereby force the liquid medication through the ampule assembly orifice, the injector assembly comprising:

(i) an injector body including a barrel closed at its back end, wherein the front end of the barrel is open and configured to receive the second end of the ampule assembly body to thereby mount the ampule assembly on the barrel;

(ii) a piston mounted for sliding movement in the barrel, the piston configured to be pushed by gas pressure from an at-rest position at the back end of the barrel toward the front end of the barrel;

(iii) a chamber in the injector body configured to house a compressed gas container;

(iv) a first passageway in the injector body through which gas flows from the gas container in the gas container chamber to the barrel to provide a force on the rearward-facing surface of the piston to move the piston toward the front end of the barrel;

(v) a second passageway in the injector body configured to be open for venting gas released from the gas container to the atmosphere when the end of the ampule assembly is not mounted in the injector assembly barrel;

(vi) means for sealing the second passageway to prevent venting gas through the passageway to the atmosphere, the seal provided only when the ampule assembly is mounted in the injector assembly barrel; and (vii) means for releasing gas from the gas container to provide the force on the rearward-facing surface of the piston to thereby move the piston toward the front end of the barrel and into contact with the plunger assembly and for moving the plunger assembly toward the orifice to thereby eject the liquid medication from the cavity out through the orifice.

29. A needleless hypodermic injection device as is claimed in claim 28 wherein the second passageway sealing means comprise:

(a) a valve stem mounted in the second passageway for sliding movement along the length of the second passageway, the valve stem being an L-shaped rod with the forward end of the valve stem having a bend extending upwardly into the opening in the front end of the injector body barrel;

(b) a valve seat at the upstream end of the second passageway; and (c) a ball located between the valve seat and the back end of the valve stem, wherein the front end of the valve stem engages the second end of the ampule assembly body as the ampule assembly body is being mounted in the barrel so that the valve stem is moved by the ampule assembly body toward the valve seat during the mounting operation, the ampule assembly holding the valve stem in place at its rearmost position when the ampule assembly end is fully mounted in the barrel to thereby trap the ball in gas-sealing engagement on the valve seat.

30. A needleless hypodermic injection device as is claimed in claim 28 wherein the gas-releasing means comprise:

(a) a actuating lever mounted on the injector body; and (b) an elongated lance having one end mounted on the actuating lever and having a point on its opposite end, the lance extending through an opening in the injector body so that:

(i) the lance point is spaced apart from and is adjacent a frangible seal on a compressed gas container positioned in the gas container chamber when the actuating lever is in its unactuated position; and (ii) the lance point is movable to a position by which it punctures the gas container seal to thereby release the gas from the container when the actuating lever is moved to its actuated position.

31. A needleless hypodermic injection device as is claimed in claim 28 which also comprises means for varying the force of the gas acting on the piston to thereby vary the velocity of the medication as it is ejected through the ampule assembly orifice.

32. A needleless hypodermic injection device as is claimed in claim 31 wherein the force-varying means comprise a gas-flow-regulator assembly comprising a disk having a plurality of gas-flow-restricting orifices of different sizes therethrough mounted in the injector body, the location of the disk being such that gas released from a gas container housed in the gas container chamber must pass through at least one such gas-flow-restricting orifice prior to contacting the piston, the flow-restricting orifices configured to be selectively positioned in the gas flow path by rotating the disk.

33. A needleless hypodermic injection device as is claimed in claim 32 wherein the disk has three sets of gas-flow-restricting orifices spaced around the perimeter, with each such orifice set being identical and each orifice being spaced apart 120° from each other orifice of the same size, the disk configured to be rotated so that in each selected position three orifices of equal size are in the gas flow path between the gas container and the piston.

34. A needleless hypodermic injection device as is claimed in claim 31 wherein the force-varying means comprise a gas-flow-regulator assembly that comprises a throttle valve having a valve seat in the gas flow path between a gas container housed in the gas container chamber and the piston, sealing means for engagement with the valve seat, a spring for biasing the sealing means on the seat, and means for varying the compression of the spring to provide a variable force for holding the sealing means on the seat.

35. A needleless hypodermic injection device as is claimed in claim 34 wherein the sealing means is a ball.

36. A needleless hypodermic injection device as is claimed in claim 28 wherein the plunger assembly has a piston on its end which moves within the ampule cavity, the piston having a groove around the circumference of its front end so that a flange is at the front-facing surface of the piston.

37. A system for injecting liquid medication through the skin of persons or animals, the system comprising a needleless hypodermic injection device and an adaptor assembly for use on a medication vial for transferring medication to the injection device;

(a) the injection device comprising:

(i) an ampule assembly comprising:

a body having a cavity for holding liquid medication between first and second ends of the body;

an orifice in the first end of the body through which such liquid medication can flow into and out from the cavity; and a plunger assembly movable within the cavity for drawing the liquid medication into the cavity and for forcing the liquid medication out from the cavity;

(ii) an injector assembly for receiving and mounting the ampule assembly and for providing a force to move the plunger assembly to thereby force the liquid medication through the ampule assembly orifice, the injector assembly comprising:

an injector body including a barrel closed at its back end, wherein the front end of the barrel is open and configured to receive the second end of the ampule assembly body to thereby mount the ampule assembly on the barrel;

a piston mounted for sliding movement in the barrel, the piston configured to be pushed by gas pressure from an at-rest position at the back end of the barrel toward the front end of the barrel;

a chamber in the injector body configured to house a compressed gas container;

a first passageway in the injector body through which gas flows from the gas container in the gas container chamber to the barrel to provide a force on a rearward-facing surface of the piston to move the piston toward the front end of the barrel;

a second passageway in the injector body configured to be open for venting gas released from the gas container to the atmosphere when the end of the ampule assembly is not mounted in the injector assembly barrel;

means for sealing the second passageway to prevent venting gas through the passageway to the atmosphere, the seal provided only when the ampule assembly is mounted in the injector assembly barrel; and means for releasing gas from the gas container to provide the force on the rearward-facing surface of the piston to thereby move the piston toward the front end of the barrel and into contact with the plunger assembly and for moving the plunger assembly toward the orifice to thereby eject the liquid medication from the cavity out through the orifice; and (b) the adaptor assembly comprising:

(i) a body having two cavities spaced apart from each other on its opposite ends, the first such cavity configured to receive the cap on a vial of liquid medication and the second such cavity configured to engage the end of an ampule assembly;

(ii) a resilient diaphragm mounted at the bottom of the second cavity, the diaphragm having a circular recess formed through a portion of its center adjacent the first cavity, and having a slit extending through its center registered with the circular recess, the slit being closed when the ampule assembly is not in the cavity, and configured to be opened by the first end of the ampule assembly when the first end of the ampule assembly is fully mounted in the cavity; and (iii) a hollow, tubular needle extending through the center of the portion of the adaptor body that separates the first and second adaptor body cavities from each other, wherein the top opening of the needle is positioned in the circular diaphragm recess with the point of the needle extending a sufficient distance into the first adaptor body cavity so that the medication vial cap is pierced by the needle when the adaptor is on the vial.

38. A system for injecting liquid medication through the skin persons or animals, the system comprising an injector assembly, an ampule assembly, an adaptor assembly for use on a medication vial for transferring medication to the ampule assembly, and a compressed gas container;

(a) the ampule assembly comprising:

(i) a body having a cavity for holding liquid medication between first and second ends of the body;

(ii) an orifice in the first end of the body through which such liquid medication can flow into and out from the cavity; and (iii) a plunger assembly movable within the cavity for drawing the liquid medication into the cavity and for forcing the liquid medication out from the cavity;

(b) the injector assembly for receiving and mounting the ampule assembly and for providing a force to move the plunger assembly to thereby force the liquid medication through the ampule assembly orifice, the injector assembly comprising:

(i) an injector body including a barrel closed at its back end, wherein the front end of the barrel is open and configured to receive the second end of the ampule assembly body to thereby mount the ampule assembly on the barrel;

(ii) a piston mounted for sliding movement in the barrel, the piston configured to be pushed by gas pressure from an at-rest position at the back end of the barrel toward the front end of the barrel;

(iii) a chamber in the injector body configured to house a compressed gas container;

(iv) a first passageway in the injector body through which gas flows from the gas container in the gas container chamber to the barrel to provide a force on the rearward-facing surface of the piston to move the piston toward the front end of the barrel;

(v) a second passageway to the injector body configured to be open for venting gas released from the gas container to the atmosphere when the end of the ampule assembly is not mounted in the injector assembly barrel;

(vi) means for sealing the second passageway to prevent venting gas through the passageway to the atmosphere, the seal provided only when the ampule assembly is mounted in the injector assembly barrel; and (vii) means for releasing gas from a gas container to provide the force on the rearward-facing surface of the piston to thereby move the piston toward the front end of the barrel and into contact with the plunger assembly and for moving the plunger assembly toward the orifice to thereby eject the liquid medication from the cavity out through the orifice;

(c) the compressed gas container provided for mounting in the injector body chamber; and (d) the adaptor assembly comprising:

(i) a body having two cavities spaced apart from each other on its opposite ends, the first such cavity configured to receive the cap on a vial of liquid medication and the second such cavity configured to engage the end of an ampule assembly;

(ii) a resilient diaphragm mounted at the bottom of the second cavity, the diaphragm having a circular recess formed through a portion of its center adjacent the first cavity, and having a slit extending through its center registered with the circular recess, the slit being closed when the ampule assembly is not in the cavity, and configured to be opened by the first end of the ampule assembly when the first end of the ampule assembly is fully mounted in the cavity; and (iii) a hollow, tubular needle extending through the center of the portion of the adaptor body that separates the first and second adaptor body cavities from each other, wherein the top opening of the needle is positioned in the circular diaphragm recess with the point of the needle extending a sufficient distance into the first adaptor body cavity so that the medication vial cap is pierced by the needle when the adaptor is on the vial.

* * * * *

UNITED STATES PATENT AND TRADEMARK OFFICE
CERTIFICATE OF CORRECTION

PATENT NO. : 5,024,656

DATED : June 18, 1991

INVENTOR(S) : Jack S. Gasaway, et al.

It is certified that error appears in the above-identified patent and that said Letters Patent is hereby corrected as shown below:

column 4, line 67, after "taken", "in" should be -- on --;
column 7, line 4, "openings" should be -- opening --;
column 7, line 7, after "plug", insert -- and --;
column 7, line 14, after "compressed", delete "air" and insert -- gas --;
column 16, line 51, "lo" should be -- 10 --;
column 23, line 1, after "receive the", insert -- second --;
column 23, line 48, after "front", insert -- end --;
column 27, line 58, "a" should be -- an --; and
column 29, line 67, after "skin", insert -- of --.

Signed and Sealed this

Twentieth Day of April, 1993

Attest:

MICHAEL K. KIRK

*Attesting Officer*  *Acting Commissioner of Patents and Trademarks*